(12) United States Patent
Zhu et al.

(10) Patent No.: US 7,931,628 B2
(45) Date of Patent: *Apr. 26, 2011

(54) DEVICE FOR CLOSING TISSUE OPENINGS

(75) Inventors: Yong Hua Zhu, Redlands, CA (US);
Wolff M. Kirsch, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 10/614,650

(22) Filed: Jul. 7, 2003

(65) Prior Publication Data
US 2004/0010216 A1    Jan. 15, 2004

Related U.S. Application Data

(63) Continuation of application No. 09/794,951, filed on Feb. 26, 2001, now Pat. No. 6,589,269.

(60) Provisional application No. 60/184,627, filed on Feb. 24, 2000.

(51) Int. Cl.
*A61F 13/00*    (2006.01)
*A61B 17/08*    (2006.01)
*A61D 1/00*    (2006.01)

(52) U.S. Cl. .................. 604/304; 606/213; 606/215

(58) Field of Classification Search .......... 604/289–290, 604/304; 606/213–215; 602/41; 128/887
See application file for complete search history.

(56) References Cited

U.S. PATENT DOCUMENTS

| 3,483,870 A | 12/1969 | Coover et al. |
| 4,394,373 A | 7/1983 | Malette et al. |
| 4,530,698 A | 7/1985 | Goldstein et al. |
| 4,532,134 A | 7/1985 | Malette et al. |
| 4,744,363 A * | 5/1988 | Hasson ........................... 606/1 |
| 4,772,266 A | 9/1988 | Groshong |
| 4,890,612 A | 1/1990 | Kensey |
| 4,921,479 A | 5/1990 | Grayzel |

(Continued)

FOREIGN PATENT DOCUMENTS

CA    2274066 C    *    6/1998

(Continued)

OTHER PUBLICATIONS

Angio-Seal, Hemostasis Puncture Closure Device Brochure, Sherwood Medical Co., Jun. 11, 1997.

(Continued)

*Primary Examiner* — Melanie J Hand
(74) *Attorney, Agent, or Firm* — Knobbe, Martens, Olson & Bear, LLP.

(57) ABSTRACT

A tissue closure device has an elongate body with a first portion and a second portion. A wound closure member is also provided. In operation, a wound closure member is releasably held on a distal end of the first portion. The wound closure member is advanced within the patient until it is placed on top of and over a wound in tissue. Flowable adhesive is injected through a lume of the second portion onto the wound closure member and tissue surrounding the wound closure member. The wound closure member applicator holds the wound closure member in place, allowing the adhesive to at least partially set. The applicator is then removed from the wound closure member. Thus, an adhesive wound closure member is attached to close an opening in tissue.

41 Claims, 22 Drawing Sheets

U.S. PATENT DOCUMENTS

| | | | |
|---|---|---|---|
| 4,961,729 A | 10/1990 | Vaillancourt | |
| 4,999,235 A | 3/1991 | Lunn et al. | |
| 5,015,249 A | 5/1991 | Nakao et al. | |
| 5,139,486 A | 8/1992 | Moss | |
| 5,176,128 A | 1/1993 | Andrese | |
| 5,192,301 A | 3/1993 | Kamiya et al. | |
| 5,192,302 A | 3/1993 | Kensey et al. | |
| 5,236,455 A * | 8/1993 | Wilk et al. | 623/10 |
| 5,257,979 A | 11/1993 | Jagpal | |
| 5,259,835 A | 11/1993 | Clark et al. | |
| 5,282,827 A | 2/1994 | Kensey et al. | |
| 5,290,310 A | 3/1994 | Makower et al. | |
| 5,292,311 A | 3/1994 | Cope | |
| 5,292,332 A | 3/1994 | Lee | |
| 5,300,065 A | 4/1994 | Anderson | |
| 5,306,259 A | 4/1994 | Fischell et al. | |
| 5,320,639 A | 6/1994 | Rudnick | |
| 5,360,397 A | 11/1994 | Pinchuk | |
| 5,370,660 A | 12/1994 | Weinstein et al. | |
| 5,383,896 A | 1/1995 | Gershony et al. | |
| 5,383,899 A | 1/1995 | Hammerslag | |
| 5,395,383 A | 3/1995 | Adams et al. | |
| 5,405,360 A | 4/1995 | Tovey | |
| 5,419,765 A | 5/1995 | Weldon et al. | |
| 5,431,639 A | 7/1995 | Shaw | |
| 5,437,631 A | 8/1995 | Janzen | |
| 5,445,597 A | 8/1995 | Clark et al. | |
| 5,458,131 A | 10/1995 | Wilk | |
| 5,480,380 A | 1/1996 | Martin | |
| 5,486,195 A | 1/1996 | Myers et al. | |
| 5,529,577 A | 6/1996 | Hammerslag | |
| 5,545,178 A | 8/1996 | Kensey et al. | |
| 5,554,118 A | 9/1996 | Jang | |
| 5,556,375 A | 9/1996 | Ewall | |
| 5,596,990 A | 1/1997 | Yock et al. | |
| 5,620,461 A | 4/1997 | Muijs Van De Moer et al. | |
| 5,632,727 A | 5/1997 | Tipton et al. | |
| 5,643,318 A | 7/1997 | Tsukernik et al. | |
| 5,645,566 A | 7/1997 | Brenneman et al. | |
| 5,649,959 A | 7/1997 | Hannam et al. | |
| 5,653,730 A | 8/1997 | Hammerslag | |
| 5,662,681 A | 9/1997 | Nash et al. | |
| 5,665,106 A | 9/1997 | Hammerslag | |
| 5,665,107 A | 9/1997 | Hammerslag | |
| 5,676,689 A | 10/1997 | Kensey et al. | |
| 5,684,042 A | 11/1997 | Greff et al. | |
| 5,725,551 A | 3/1998 | Myers et al. | |
| 5,728,114 A | 3/1998 | Evans | |
| 5,728,132 A | 3/1998 | Van Tassel et al. | |
| 5,759,169 A | 6/1998 | Marx | |
| 5,759,194 A * | 6/1998 | Hammerslag | 606/214 |
| 5,776,096 A | 7/1998 | Fields | |
| 5,810,810 A | 9/1998 | Tay et al. | |
| 5,810,884 A * | 9/1998 | Kim | 606/213 |
| 5,811,091 A | 9/1998 | Greff et al. | |
| 5,836,970 A | 11/1998 | Pandit | |
| 5,843,124 A | 12/1998 | Hammerslag | |
| 5,876,387 A | 3/1999 | Killian et al. | |
| 5,895,412 A | 4/1999 | Tucker | |
| 5,906,631 A | 5/1999 | Imran | |
| 5,910,155 A | 6/1999 | Ratcliff et al. | |
| 5,928,266 A | 7/1999 | Kontos | |
| 5,944,730 A | 8/1999 | Nobles et al. | |
| 5,971,956 A | 10/1999 | Epstein | |
| 6,004,341 A | 12/1999 | Zhu et al. | |
| 6,007,563 A * | 12/1999 | Nash et al. | 606/213 |
| 6,048,358 A * | 4/2000 | Barak | 606/213 |
| 6,056,768 A | 5/2000 | Cates et al. | |
| 6,155,265 A | 12/2000 | Hammerslag et al. | |
| 6,159,178 A | 12/2000 | Sharkawy et al. | |
| 6,198,016 B1 | 3/2001 | Lucast et al. | |
| 6,287,322 B1 | 9/2001 | Zhu et al. | |
| 6,287,323 B1 * | 9/2001 | Hammerslag | 606/214 |
| 6,315,753 B1 | 11/2001 | Cragg et al. | |
| 6,346,093 B1 | 2/2002 | Allman et al. | |
| 6,371,974 B1 | 4/2002 | Brenneman | |
| 6,425,901 B1 | 7/2002 | Zhu et al. | |
| 6,508,828 B1 | 1/2003 | Akerfeldt et al. | |
| 6,524,326 B1 | 2/2003 | Zhu et al. | |
| 6,589,269 B2 * | 7/2003 | Zhu et al. | 606/214 |
| 6,613,070 B2 | 9/2003 | Redmond et al. | |
| 6,890,342 B2 | 5/2005 | Zhu et al. | |
| 6,964,675 B2 | 11/2005 | Zhu et al. | |
| 2001/0004710 A1 | 6/2001 | Felt et al. | |
| 2001/0018598 A1 | 8/2001 | Cruise et al. | |
| 2002/0077656 A1 | 6/2002 | Ginn et al. | |
| 2002/0147479 A1 | 10/2002 | Aldrich | |
| 2003/0050665 A1 | 3/2003 | Ginn | |
| 2003/0109820 A1 | 6/2003 | Gross et al. | |
| 2006/0100664 A1 | 5/2006 | Pai et al. | |

FOREIGN PATENT DOCUMENTS

| | | |
|---|---|---|
| CA | 2334226 | 4/2005 |
| CA | 2274066 | 2/2006 |
| DE | EP 0 482 350 A2 * | 4/1992 |
| EP | 0 028 452 A1 | 5/1981 |
| EP | 0 745 350 A1 | 12/1996 |
| EP | 0 955 900 | 7/2005 |
| FR | 2574285 A1 | 6/1986 |
| WO | WO 94/21306 | 9/1994 |
| WO | WO 95/05206 | 2/1995 |
| WO | WO 96 10374 A1 | 4/1996 |
| WO | WO 96 24291 A1 | 8/1996 |
| WO | WO 97 20505 A1 | 6/1997 |
| WO | WO 98 24374 A1 | 6/1998 |
| WO | WO 99 22646 A1 | 5/1999 |
| WO | WO 99 42535 A1 | 8/1999 |
| WO | WO 99/62405 | 12/1999 |
| WO | WO 00/02488 | 1/2000 |
| WO | WO 00/07640 | 2/2000 |
| WO | WO 00 19912 A1 | 4/2000 |
| WO | WO 00 33744 A1 | 6/2000 |
| WO | WO 01 62159 A2 | 8/2001 |
| WO | WO 02/05865 A2 | 1/2002 |
| WO | WO 02 09591 A2 | 2/2002 |
| WO | WO 03 008002 A1 | 1/2003 |
| WO | WO 03 008003 A1 | 1/2003 |

OTHER PUBLICATIONS

Medafor, Inc. Adds Two management Team Members, Press Release, Jun. 7, 2001, http://www.medafor.com/news0601.html.

* cited by examiner

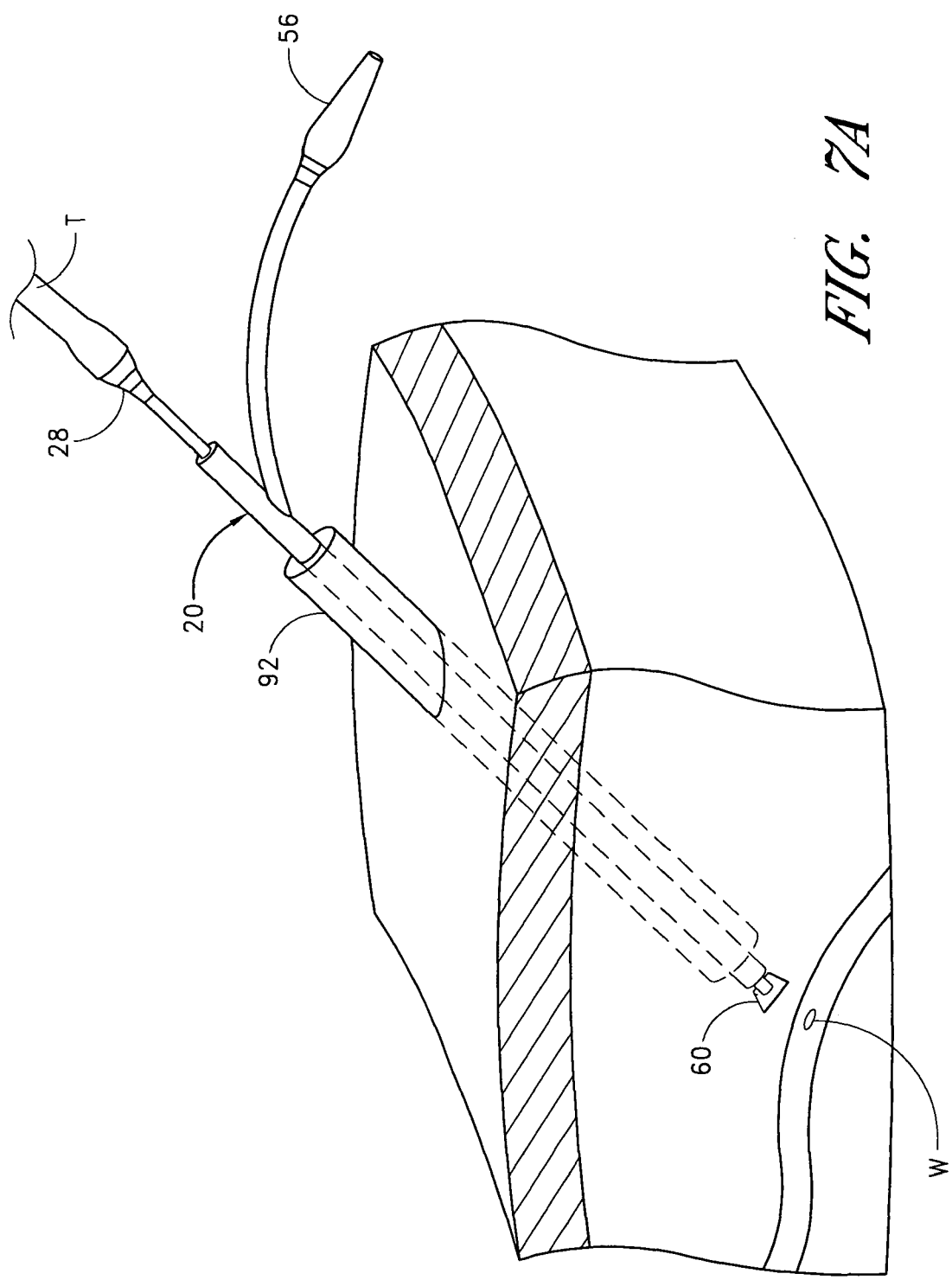

DEVICE FOR CLOSING TISSUE OPENINGS

RELATED APPLICATIONS

This application is a continuation of U.S. application Ser. No. 09/794,951, filed Feb. 26, 2001 now U.S. Pat. No. 6,589,269, which claims priority to Provisional Application No. 60/184,627, filed Feb. 24, 2000. The entirety of both priority applications are hereby incorporated by reference.

BACKGROUND OF THE INVENTION

1. Field of the Invention

This invention relates to a tissue closure device and more specifically to a device and method for applying a wound closure member with flowable adhesive to close an opening in tissue during surgical procedures.

2. Description of the Related Art

Many medical procedures require closure of subcutaneous openings in tissues. In an effort to minimize patient trauma, many types of surgeries are typically performed through as small of an incision as possible. This arrangement may cause closure of internal wounds within the patient to be problematic and difficult. If such a subcutaneous wound cannot be effectively and confidently closed, the clinician must enlarge the incision or make a new incision in order to gain sufficient access to the tissue to enable closure of the wound through traditional open-surgery techniques such as suturing or clips.

In an effort to minimize patient trauma, many types of surgeries are typically performed through as small of an incision as possible. Endoscopic surgery typically uses a cannula or trocar inserted through a relatively small incision through the patient's outer tissue layers to provide access to the patient's internal organs. Insertion and removal of tools through the trocar is difficult, time-consuming and inconvenient for the clinician. Thus, a limitation of endoscopic surgery is that it is relatively difficult to use multiple tools to effect wound closure.

Internal tissue wounds present unique problems that must be addressed when attempting to close such wounds. For example, bleeding within the field around the wound can make the wound difficult to locate and can also be life-threatening to the patient. Also, since access to an internal wound is typically achieved through a trocar or the like, there are limits to the number of instruments that can be used simultaneously during surgery. As a result, surgical instruments may be called upon to perform tasks without the aid of other instruments. However, consistent and reliable closure of a wound using only a single instrument is difficult to achieve.

SUMMARY OF THE INVENTION

Accordingly, there is a need in the art for a single surgical instrument that can access internal wounds through a confined space, locate the wound and close the wound.

In accordance with one embodiment of the present invention, a wound closure device is provided. The device includes an elongate body having a first elongate portion and a second elongate portion. Each elongate portion has a distal end. The elongate portions are arranged generally adjacent one another so that the first portion distal end is disposed a minimum distance distal of the second portion distal end. A patch is releasably connected to the first portion distal end. The second elongate portion has a lumen. A lumen distal opening is at the second portion distal end. The second portion lumen distal opening is spaced from the patch.

In accordance with further embodiments, the present invention additionally includes features such as a release rod and an organ stabilizer. The release rod is adapted to fit through a lumen. The organ stabilizer is adapted to releasably hold onto bodily tissue For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 7a is a perspective view showing the patch applicator device of FIG. 1 inserted through a trocar positioned through a patient's body tissue.

DETAILED DESCRIPTION OF THE PREFERRED EMBODIMENT

Figure 1:
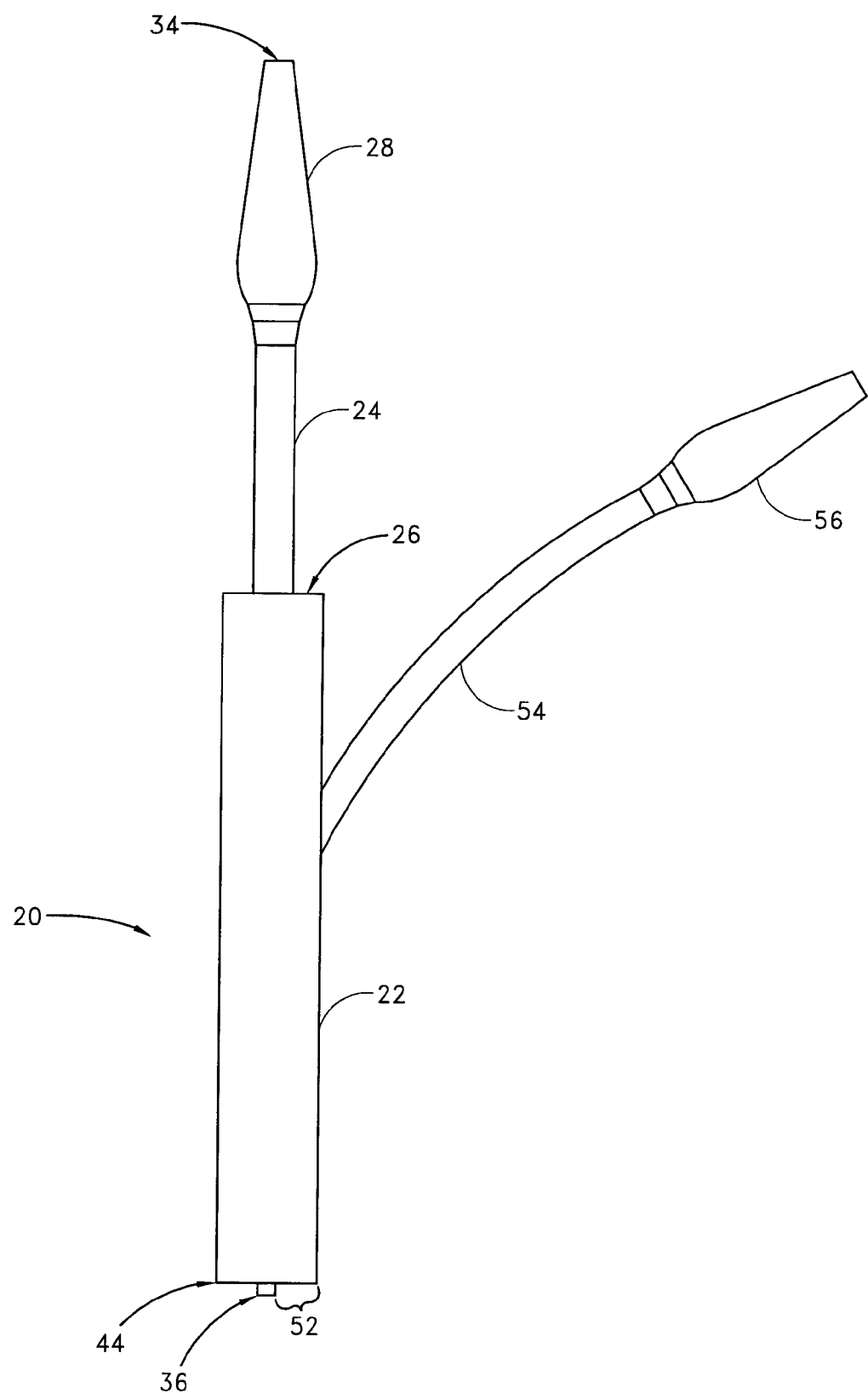
FIG. 1 is a side view of a patch applicator device having features in accordance with the present invention.
Figure 2:
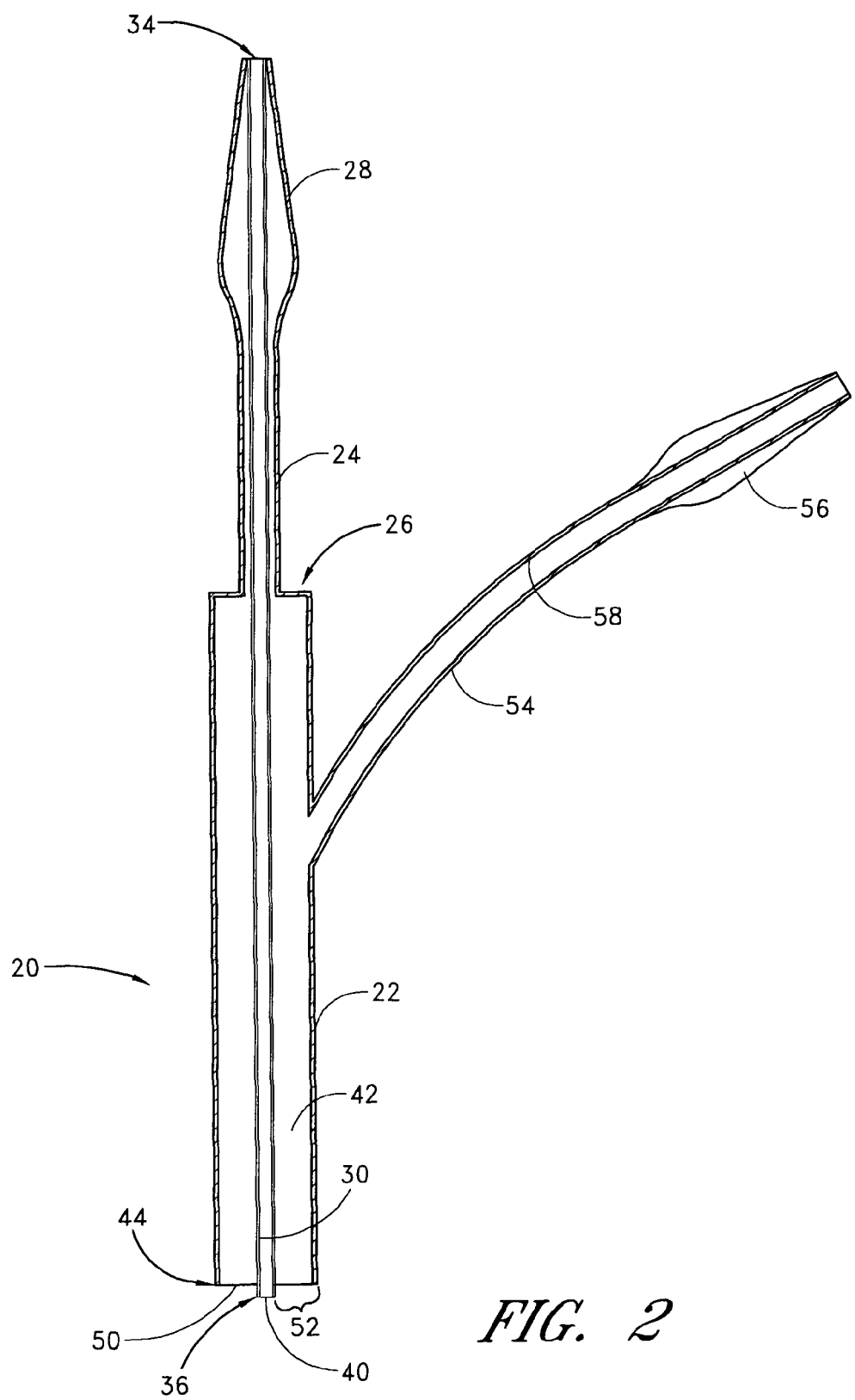
FIG. 2 is a cross-sectional view of the patch applicator of FIG. 1.

With reference first to FIGS. 1 and 2, the patch applicator device 20 of the present invention includes a tubular main body 22. A first neck 24 extends from the proximal end 26 of the tubular main body 22 and terminates in a first connector 28. The first connector 28 is preferably adapted to connect to various medical devices, such as vacuum tubing. An inner lumen 30 extends from the proximal tip 34 of the first connector 28 through the first neck 24 and the main body 22 and terminates at a distal tip 36. An inner lumen distal opening 40 is located at the distal tip 36 of the inner lumen 30.

An outer lumen 42 is defined within the tubular body 22 and preferably concentrically surrounds the inner lumen 30. The outer lumen 42 extends from the proximal end 26 of the main body 22 to a distal tip 44 of the tubular body 22, terminating at an outer lumen distal opening 50. The inner lumen distal tip 36 extends a short distance beyond the main body distal tip 44 and a space 52 is defined between the outer lumen distal opening 50 and the inner lumen distal opening 40.

A second neck 54 extends from the main body 22 and terminates in a second connector 56. The second connector 56 is adapted to receive various medical devices, such as vacuum tubing or a syringe barrel. A lumen 58 is defined through the second connector 56 and second neck 54 and communicates with the outer lumen 42.

Figure 3:
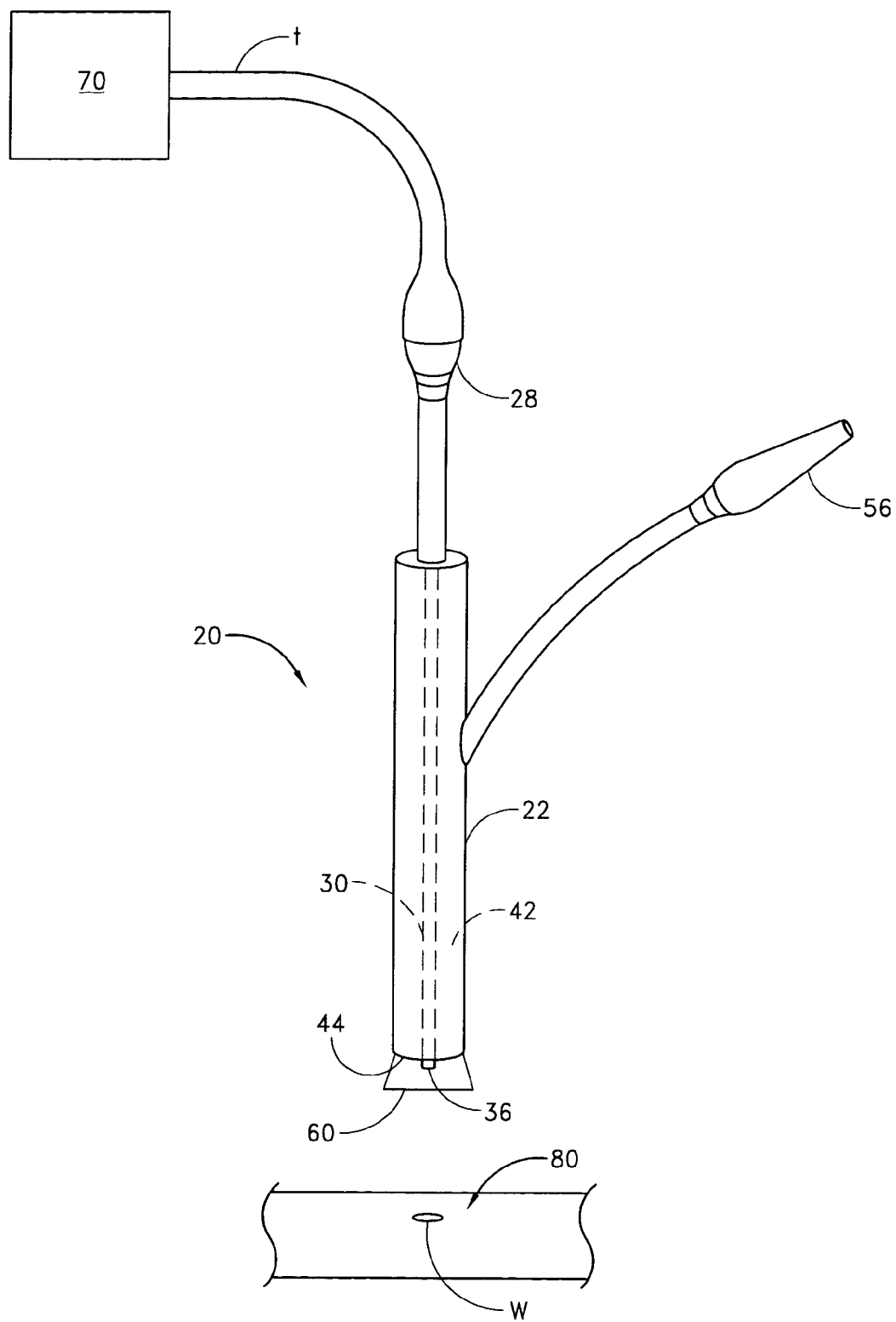
FIG. 3 is a perspective view of the patch applicator device of FIG. 1 shown connected to a source of vacuum and suspended over a wound in tissue.

As shown in FIG. 3, the patch applicator device 20 is adapted to releasably hold a patch 60 in order to position the patch on top of a wound W in tissue, and to direct a flow of adhesive A (see FIG. 5) onto the patch and the surrounding tissue in order to close the wound. A source of vacuum 70 is preferably connected to vacuum tubing "t" which, in turn, is attached to the first connector 28. A vacuum is thus created through the inner lumen 30, turning the inner lumen distal opening 40 into a vacuum port. When the inner lumen distal opening 40 is brought into contact with the patch 60, the patch is held by the vacuum on the inner lumen distal tip 36.

The patch 60 is adapted to cover an opening in body tissue and may be shaped in any desired geometry and formed from any suitable patch material, such as PTFE, biovascular material, collagen, Gore-Tex®, Dacron™, etc. The patch may also be formed out of materials that will dissolve over time within the patient's body.

FIGS. 3-7 show an operational example of an embodiment of the present device 20 being used to close a wound W in internal bodily tissue. The following discussion uses the example of closing an internal vascular wound; however, the patch applicator device may be used to close any type of internal wound such as wounds to the intestines, stomach, lungs, or other internal organs.

Prior to positioning the patch 60 on the applicator 20, the patch is preferably cut to an appropriate shape to roughly approximate the size and shape of the wound W to be closed.

The vacuum source 70 is then connected to the first connector 28, thus drawing a vacuum through the inner lumen 30. The inner lumen distal tip 36 is brought into contact with the patch 60 and the vacuum holds the patch 60 in place on the inner lumen distal tip 36, as shown in FIG. 3.

Figure 4:
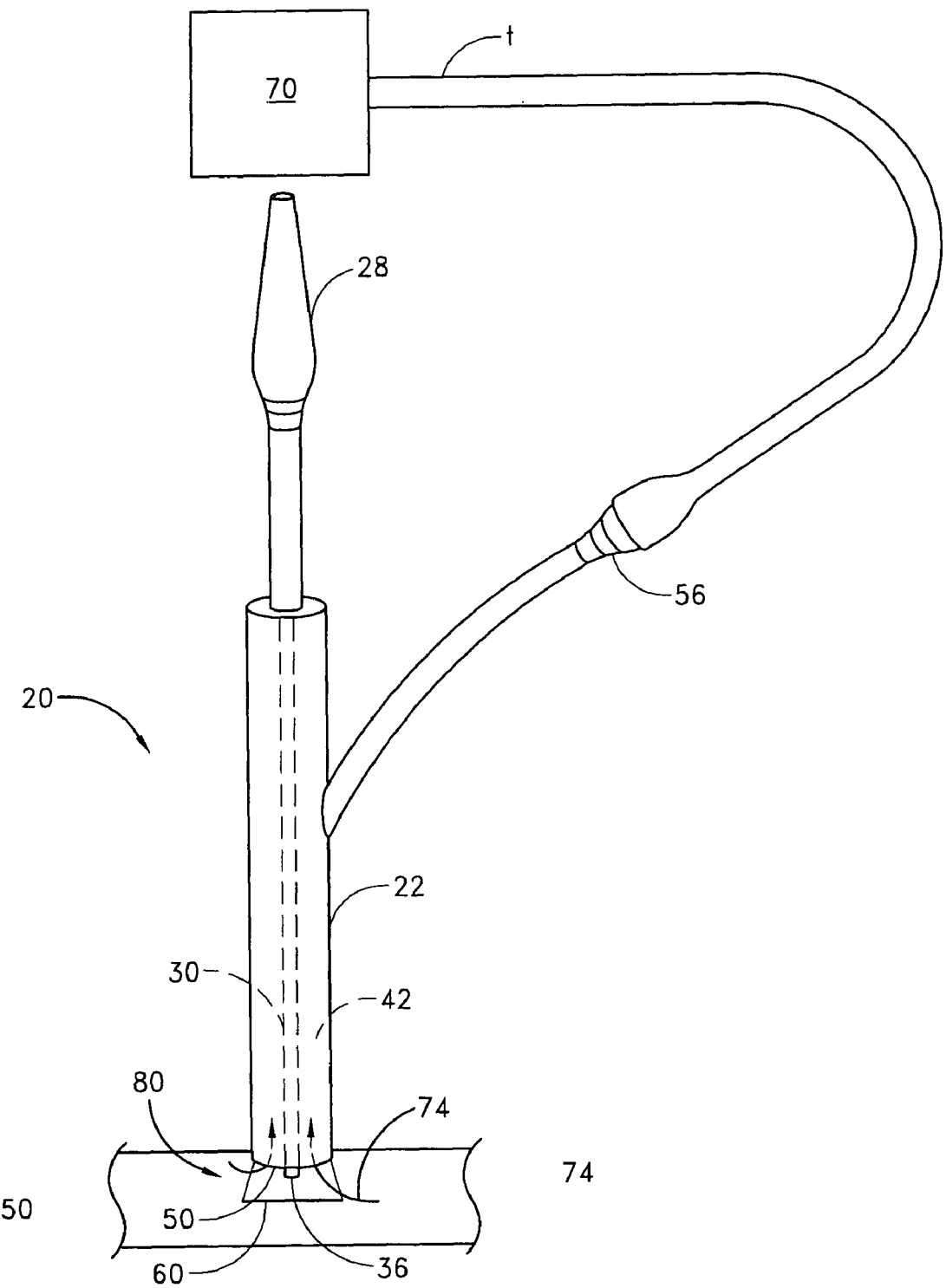
FIG. 4 shows the arrangement of FIG. 3, wherein the patch applicator device is being used to clear the field around the wound.

A wound in a blood vessel is typically surrounded by blood or bodily fluid 74, which collects in a field area 80 defined immediately around the wound. With reference to FIG. 4, the patch 60 is advanced to cover and apply pressure to the wound, even if there is bodily fluid 74 in the field. With the patch 60 in place, covering the wound, the clinician maintains pressure in order to stop additional bleeding. A source of vacuum is connected to the second connector 56, creating a suction through the outer lumen distal opening 50. The vacuum can be provided by moving the vacuum tubing "t" from the first connector 28 to the second connector 56, or by providing another source of vacuum.

When suction is being pulled through the outer lumen distal opening 50, the space 52 between the inner lumen distal tip 36 and outer lumen distal opening 50 allows blood or other bodily fluid 74 to be sucked through the outer lumen distal opening 50, thus clearing the field 80 while still holding the patch 60 in place.

Clearing the field 80 has certain advantages, including allowing space for adhesive to appropriately bond to the tissue surrounding the wound W and patch 60, minimizing the chance for later infection, and allowing the clinician to better observe the wound-closing process. During clearing of the field 80, the clinician preferably maintains pressure on the patch applicator so that the patch is held in its position over the wound.

Figure 4A:
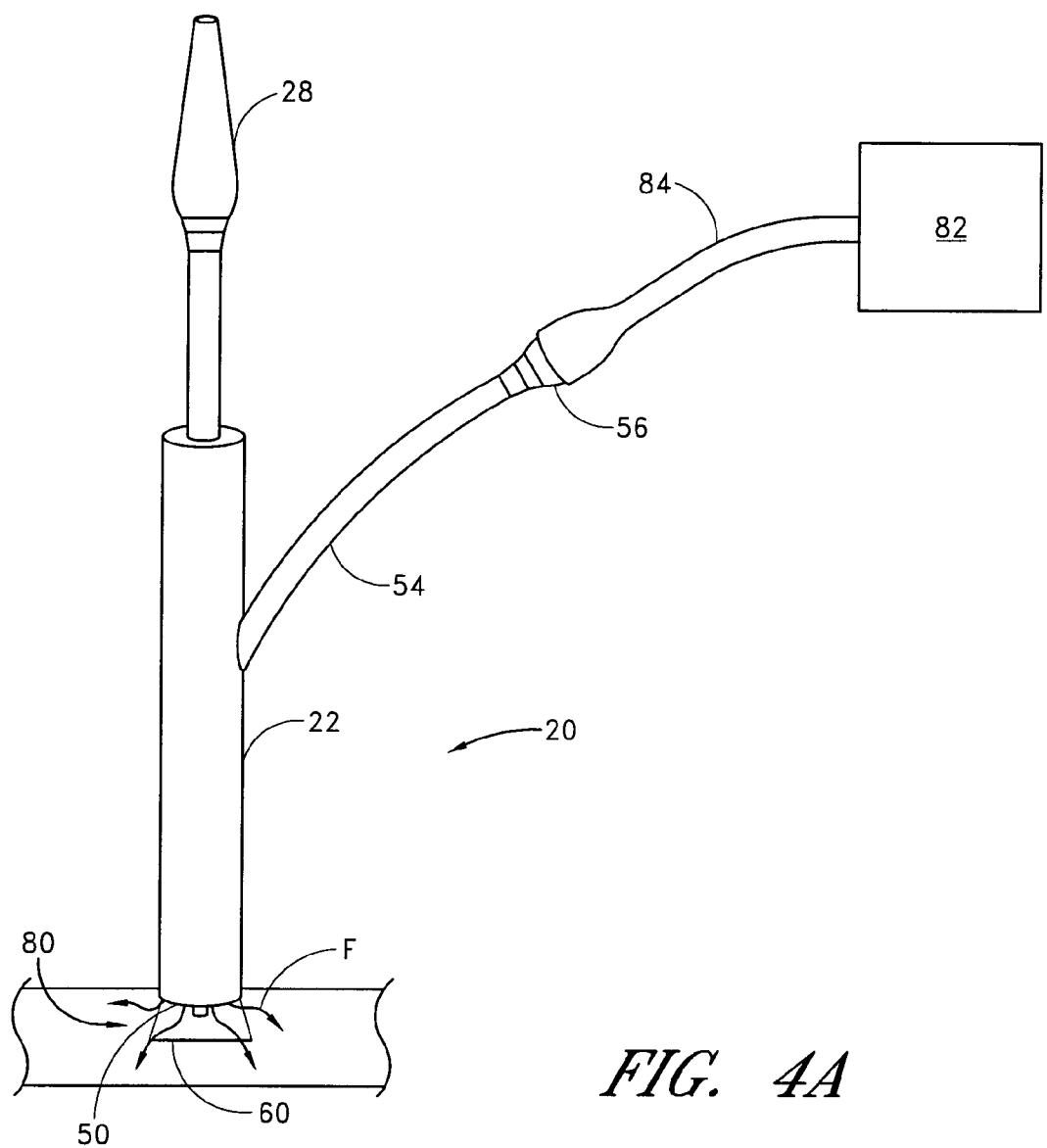
FIG. 4a shows the arrangement of FIG. 3, wherein the patch applicator device is connected to a source of irrigation fluid.

FIG. 4a shows an additional method and apparatus for clearing the field 80. As shown, a source of irrigating fluid 82 is connected through tubing 84 to the second connector 56. Irrigating fluid F is inserted through the second neck 54 into the outer lumen 42 and through the outer lumen distal opening 50 into the field 80. The irrigating fluid F irrigates the field 80. This method and apparatus may be used in lieu of the vacuum for clearing the field. However, irrigation is preferably used in conjunction with the vacuuming method shown in FIG. 4. For instance, the source of vacuum 70 can first be used to clear the field 80; however, certain thick blood and other bodily fluids 74 may remain in the field. At this time, the vacuum tubing "t" can be removed from the second connector 56 and the irrigating tubing 84 connected. As irrigating fluid F is injected into the field 80, the fluid F will dilute and clean the contents of the field. The vacuum tubing "t" can then be reattached to the second connector 56 and the field 80 again cleared by drawing irrigating fluid and bodily fluids through the outer lumen distal opening 50.

Figure 5:
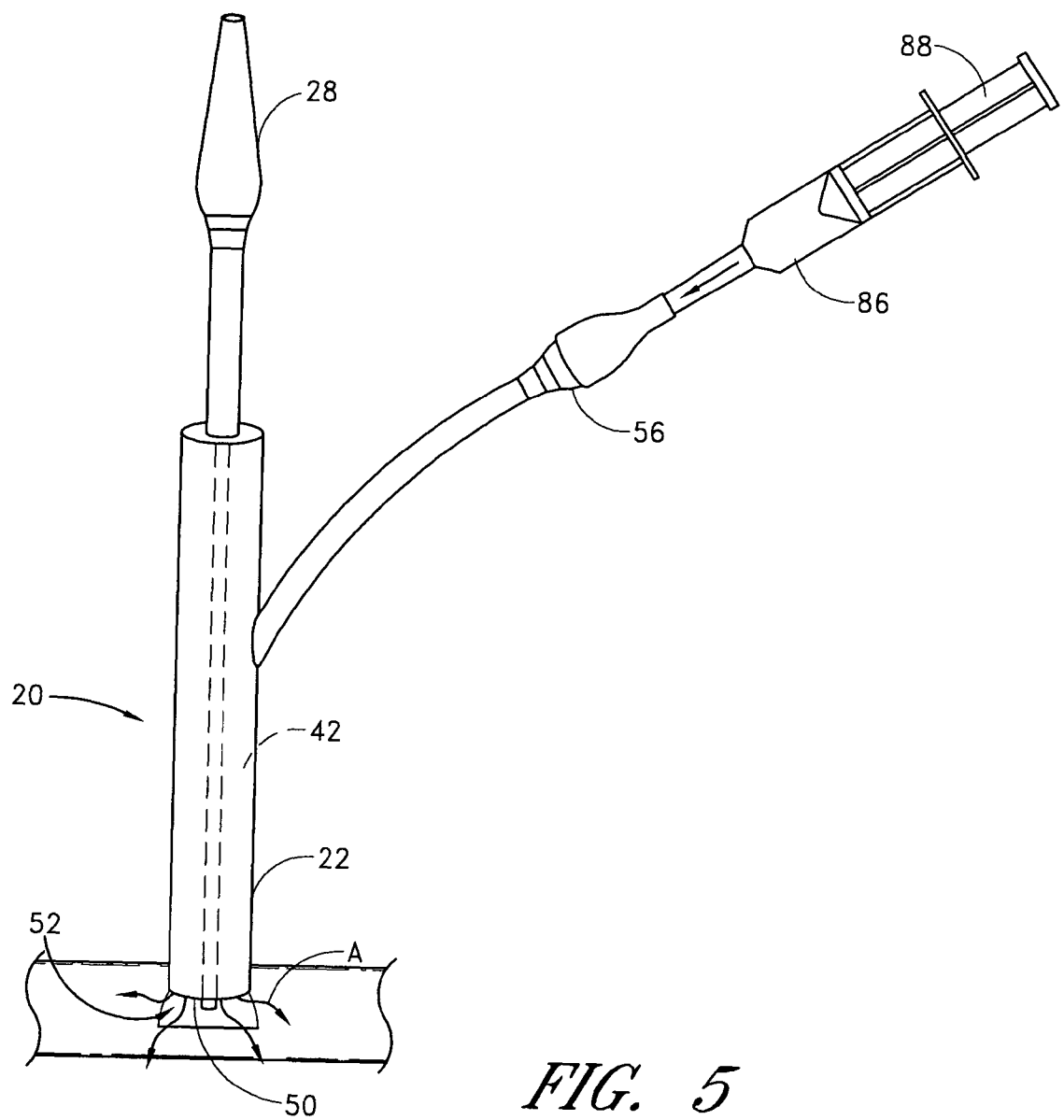
FIG. 5 shows the arrangement of FIG. 3, wherein the flowable adhesive is being applied about the patch.

With reference next to FIG. 5, once the field is cleared, the vacuum tubing is removed from the second connector and replaced with a syringe 86 filled with a flowable adhesive A. When the syringe plunger 88 is actuated, adhesive A is forced into the outer lumen 42, through the outer lumen distal opening 50 and into contact with the patch 60 and the tissue surrounding the patch. The adhesive A is directed radially outwardly through the space 52 between the inner lumen distal tip 36 and main body distal tip 44. The volume of adhesive A delivered is dictated by the size of the patch and wound. Adhesive A should fully cover at least the edges of the patch 60.

Various kinds of flowable adhesives may be acceptable for use with the patch. For example, fibrin tissue sealants such as Tisseel®, which is available from Baxter Healthcare Corp., may be appropriate. Other commercially available adhesives that may be appropriate include Bioglue™, available from Cryolife, Inc., and Floseal™, which is available from Fusion Medical Technologies. Various cyanoacrylate adhesives are currently commercially available and can be used with this invention. Of course, any product that is capable of sealing the patch onto body tissue would be acceptable. It is also to be understood that certain adhesives will not require that the field and/or the outer wall of the blood vessel be cleared before the adhesive is injected.

After adhesive A has been applied to the patch and tissue surrounding the patch, the patch applicator 20 holds the patch in place while the adhesive sets. The adhesive preferably takes about 30 seconds to set; however, this time period may vary according to the adhesive used. Once the adhesive has set, the patch can be held in place by the adhesive, and pressure on the patch can be released.

Figure 6:
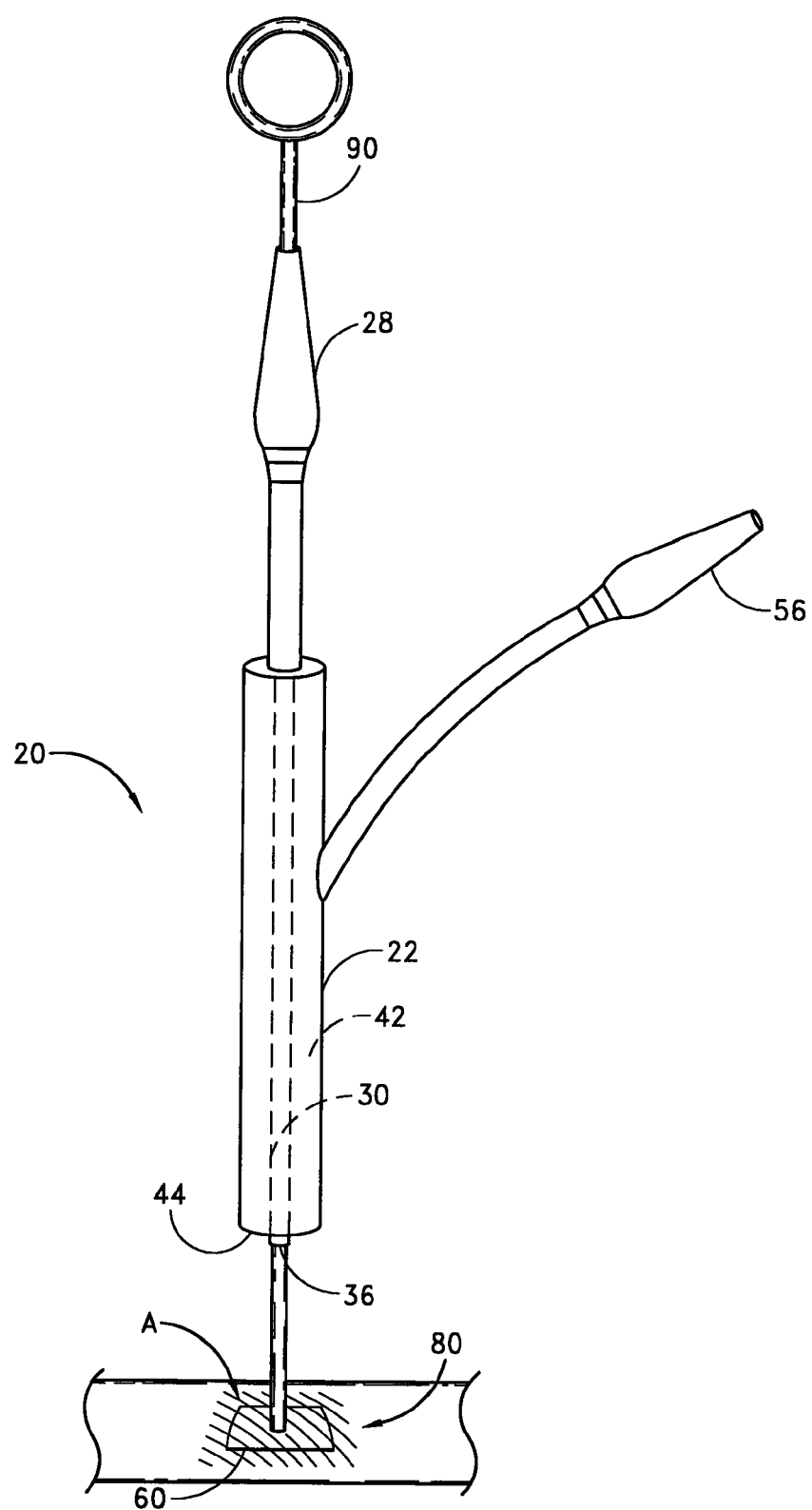
FIG. 6 shows the arrangement of FIG. 5, wherein the applicator device has been removed from the patch with the help of a release rod.

With reference next to FIG. 6, a release rod 90 can be inserted through the first connector 28, through the inner lumen 30 and out of the inner lumen distal opening 36. The release rod 90 comes into contact with the patch 60 and helps hold the patch 60 in place. If the adhesive A has partially bonded to the patch applicator 20, the release rod will hold the patch in place while the applicator 20 is removed. This will prevent or minimize the likelihood that the patch 60 will be pulled from its placement or damaged when the applicator 20 is withdrawn.

The release rod 90 generally has a smaller diameter than the patch applicator's inner lumen distal opening 36. Thus, if the patch applicator 20 is removed from the patch 60 before the adhesive sets completely, the portion of flowable adhesive that has not yet set will flow about the release rod 90, effectively covering more of the patch than was available for coverage while the patch applicator was still in contact with the patch. The release rod 90 maintains pressure on the patch while the adhesive A sets. If the adhesive should at least partially bond to the release rod, the patch applicator may be advanced again into contact with the set adhesive to provide counter traction, enabling the release rod to be withdrawn from the patch 60 without damaging the patch seal.

Figure 7:
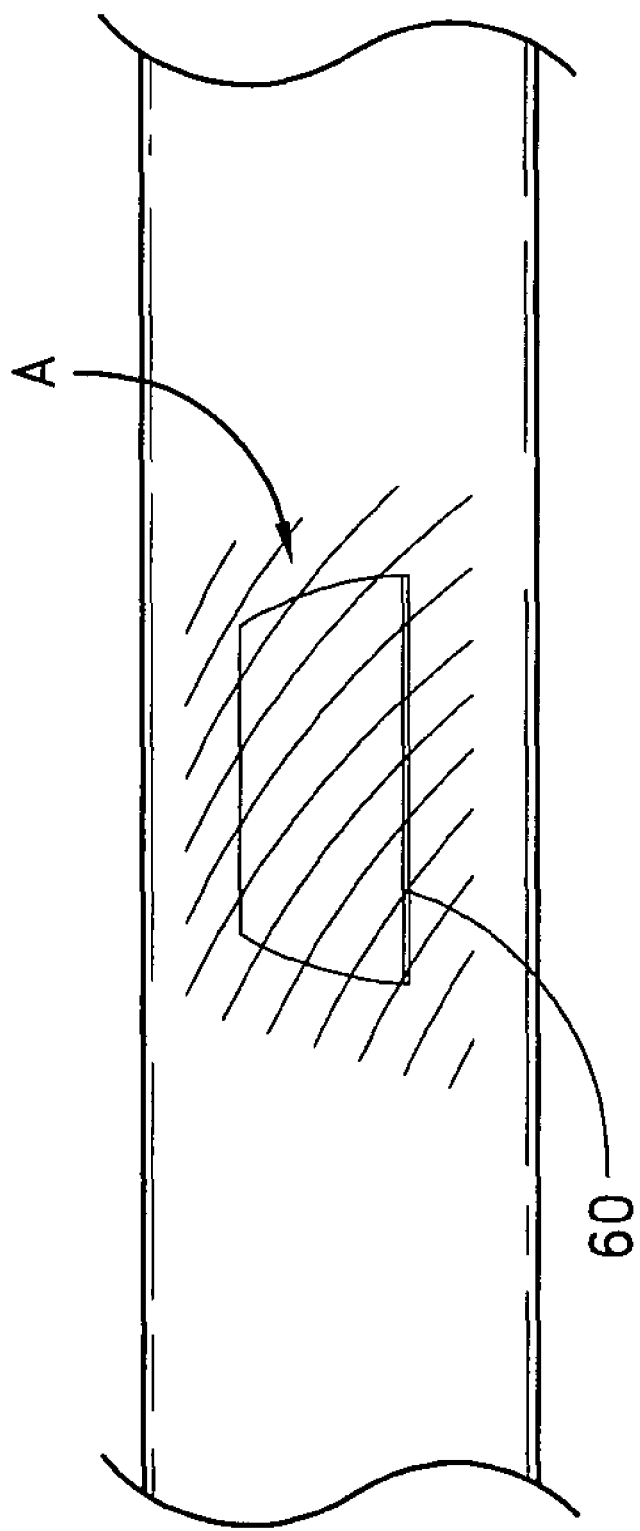
FIG. 7 shows the internal wound of FIG. 3 after being closed and after the patch applicator device has been removed.

With reference to FIG. 7, once the adhesive A sets, the release rod is removed from the patch 60 along with the patch applicator device. The patch 60 remains fixed by the adhesive to the tissue surrounding the wound and holds the wound closed.

It is to be understood that the release rod may be advanced into contact with the patch any time after the patch has been applied to the wound. For example, the release rod may be advanced prior to clearing of the field, immediately before or after injection of adhesive, or after the adhesive has begun to set, as discussed above.

When the release rod is in place, the patch applicator may be removed from direct contact with the patch. Thus, when clearing the field, the release rod may hold the patch in place while the patch applicator is removed a short distance from the patch in order to improve vacuum and irrigating fluid access to the field around the wound.

In another embodiment, after the patch 60 has been applied to the wound W and the field 80 about the patch has been cleared, the release rod 90 may be advanced to hold the patch in place. The applicator 20 is then removed from the patch a short distance and adhesive A is injected. The additional space between the outer lumen distal opening and the patch will encourage broader distribution of the adhesive. This may be advantageous in certain applications.

The patch applicator apparatus and method of the present invention is particularly advantageous for use in endoscopic applications because a single apparatus is used to hold and apply the patch, clear the field, apply the adhesive, and remove the applicator. As shown in FIG. 7a, the patch applicator device 20, including the patch 60, can be inserted through a trocar 92 or through a limited-access surgical incision in order to access a subcutaneous wound W.

The patch 60 is applied to the wound W before any adhesive is injected; thus, the wound is closed without adhesive penetrating into the wound. This is particularly advantageous because adhesives may have a level of toxicity. Accordingly, it is advantageous to minimize adhesive access to the area inside the wound. Since no adhesive enters the wound, there is very little chance that adhesive will leak into the wound and cause blockages within the closed tissue. For example, there is little risk of adhesive blockages forming in the vasculature of the patient when a blood vessel wound is closed by the present device. Similarly, there is little risk of clumps of adhesive causing blockages in the patient's lungs or digestive system when the present patch and applicator are used to close wounds in these systems.

During endoscopic or minimally-invasive surgery, if the clinician finds or causes a hemorrhage resulting in significant bleeding, the clinician must typically convert the endoscopic procedure to open surgery. This conversion includes a rush to open the chest or abdominal wall of the patient to gain access to the hemorrhage in order to close the hemorrhage with traditional surgical techniques such as clipping and suturing. Opening the chest or abdominal wall of the patient takes significant time. Depending upon the skill of the surgeon, this time may range from about three to four minutes to several minutes. During this time, bleeding continues unchecked, causing the patient to lose significant quantities of blood and possibly placing the patient's life in danger. The patch applicator device 20 is particularly advantageous in such emergency situations because instead of requiring the clinician to convert to an open surgery procedure, the patch applicator may be inserted into the patient through a trocar and the surgeon may immediately use the applicator to apply pressure on the hemorrhage, stopping blood flow. The hemorrhage can then be closed in a manner similar to that discussed above. Thus, not only has the clinician avoided having to convert to open surgery, which significantly increases the scarring, pain and risks to the patient, but also bleeding is stopped faster than is possible by converting to open surgery. The patient is saved from significant blood loss and the patient's life is not placed in the danger that is inherent in surgical conversion.

The patch applicator device may include accessories to improve its use in certain endoscopic situations. For example, to close certain wounds in tissues, the only access available for the device may be at an angle rather than from directly above the wound. This may present a problem when flowable adhesive is used, because the flowable adhesive will tend to flow downward with gravity. As a result, areas of the patch which are located vertically above the outer lumen distal opening may not be adequately covered with adhesive, resulting in an inadequate bond of the patch to the surrounding tissue.

Figure 8:
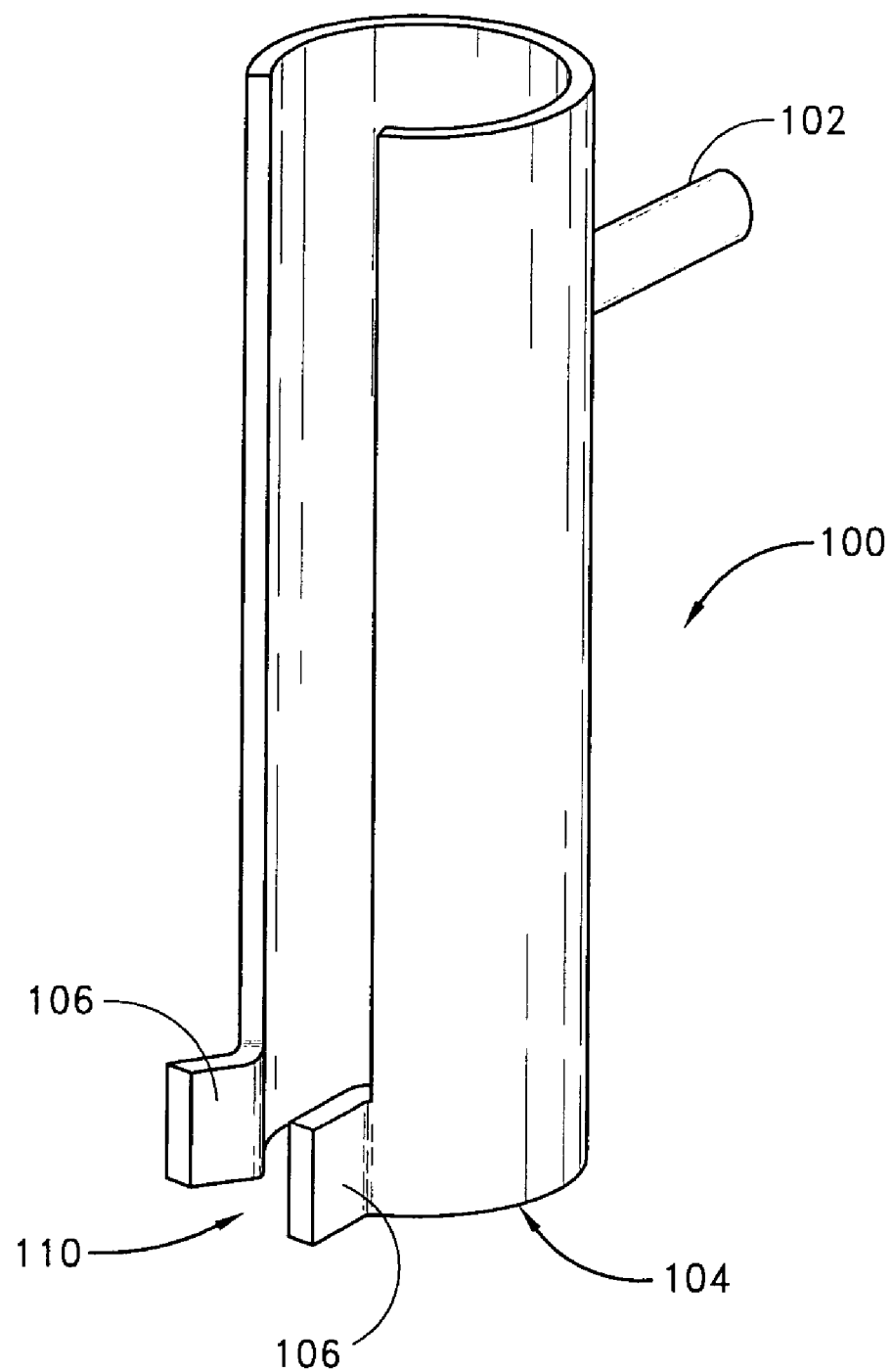
FIG. 8 shows a flow guide adapted to be used with the patch applicator device of FIG. 1.
Figure 9:
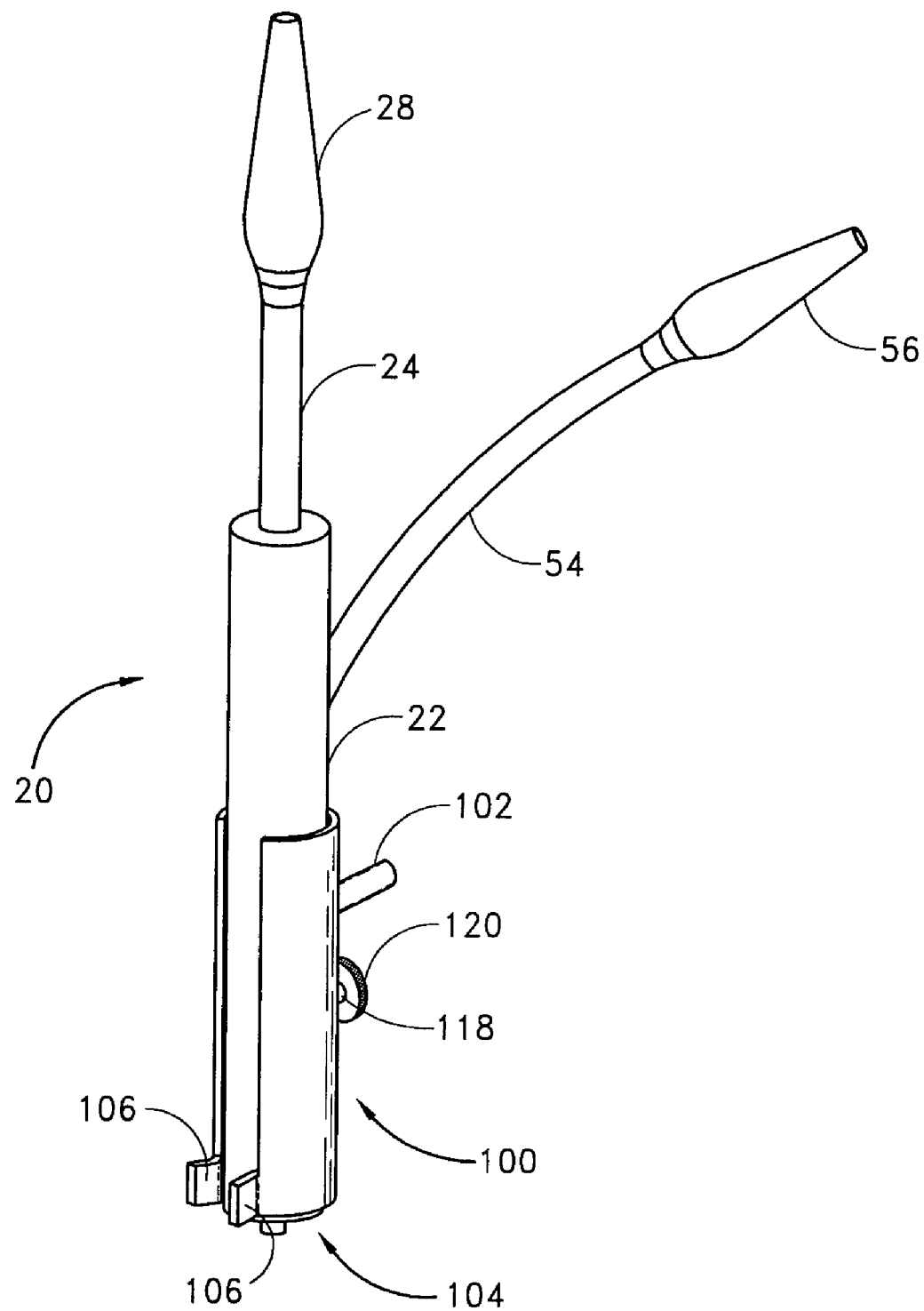
FIG. 9 shows the patch applicator device in combination with the flow guide of FIG. 8.

FIG. 8 shows a flow guide 100 adapted for use with the patch applicator 20 in order to direct adhesive A in desired directions. The flow guide 100 preferably has a substantially circular, though partially cut away, cross-section throughout most of its length. As shown in FIG. 9, the main body 22 of the patch closure device 20 preferably has a circular cross-section. The cross-section of the flow guide 100 is preferably adapted so that the flow guide 100 can snap onto the main body 22 and be slidable relative to the main body 22.

A handle 102 extends from the flow guide 100 near a proximal end thereof. The handle 102 helps the user control the sliding of the flow guide 100 relative to the main body 22. The distal tip 104 of the flow guide 100 includes a pair of guide tabs 106. The guide tabs 106 extend outwardly from the flow guide 100. A flow path is defined between the guide tabs.

Figure 10:
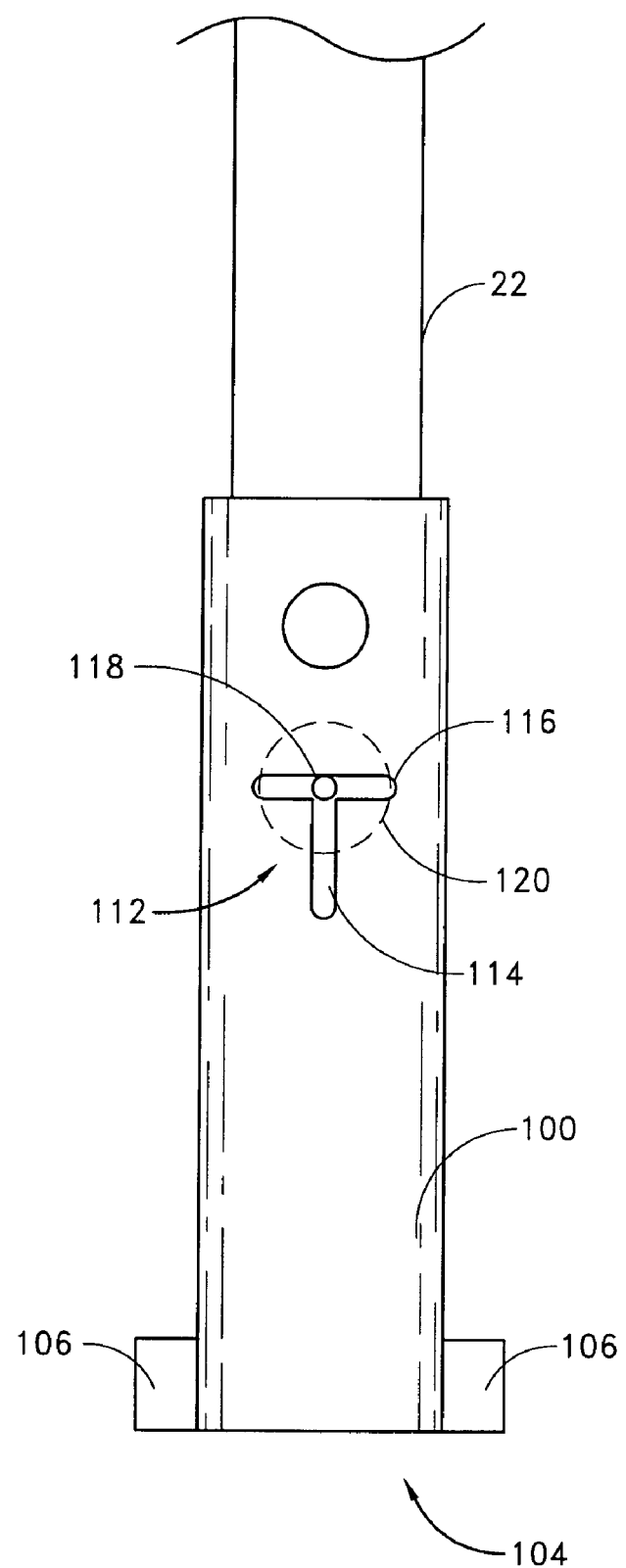
FIG. 10 shows a back view of the apparatus of FIG. 9.

With reference to FIGS. 9 and 10, a slot 112 is defined in a back side of the flow guide 100. The slot 112 preferably has a longitudinal track 114 and a transverse track 116. A pin 118 extends from the main body 22, through the slot 112, and is joined to a knob 120. The knob 120 and pin 118 are configured so that the knob 120 tightens as it is rotated. In this arrangement, the flow guide 100 may be moved relative to the applicator 20, but is constrained by the pin 118 to the range of movement allowed by the slot 112. The position of the flow guide 100 relative to the main body 22 may be secured by twisting the knob 120 when the flow guide is in a desired position.

Figure 11:
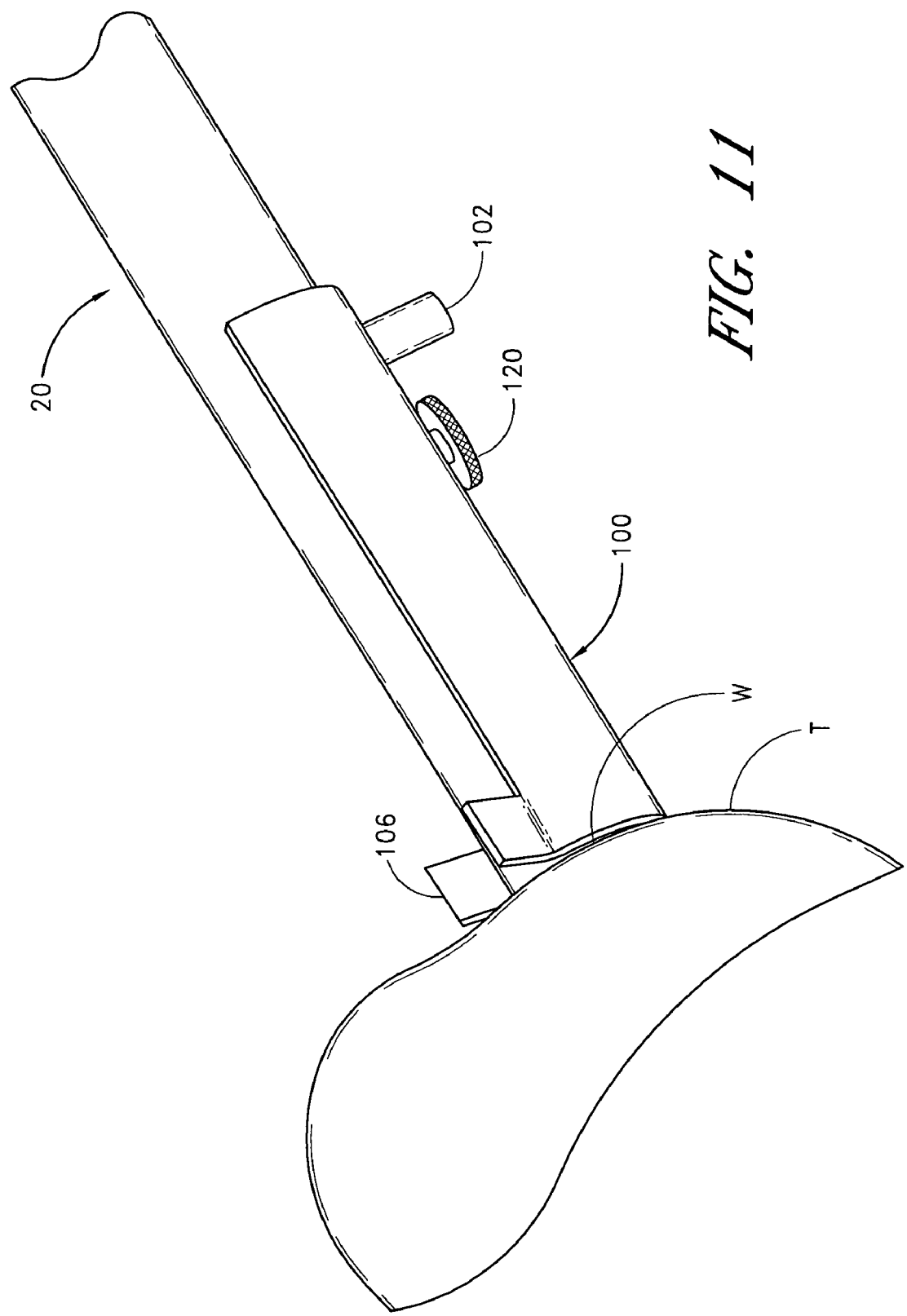
FIG. 11 shows the apparatus of FIG. 9 applied at an angle to a wound in tissue.
Figure 12:
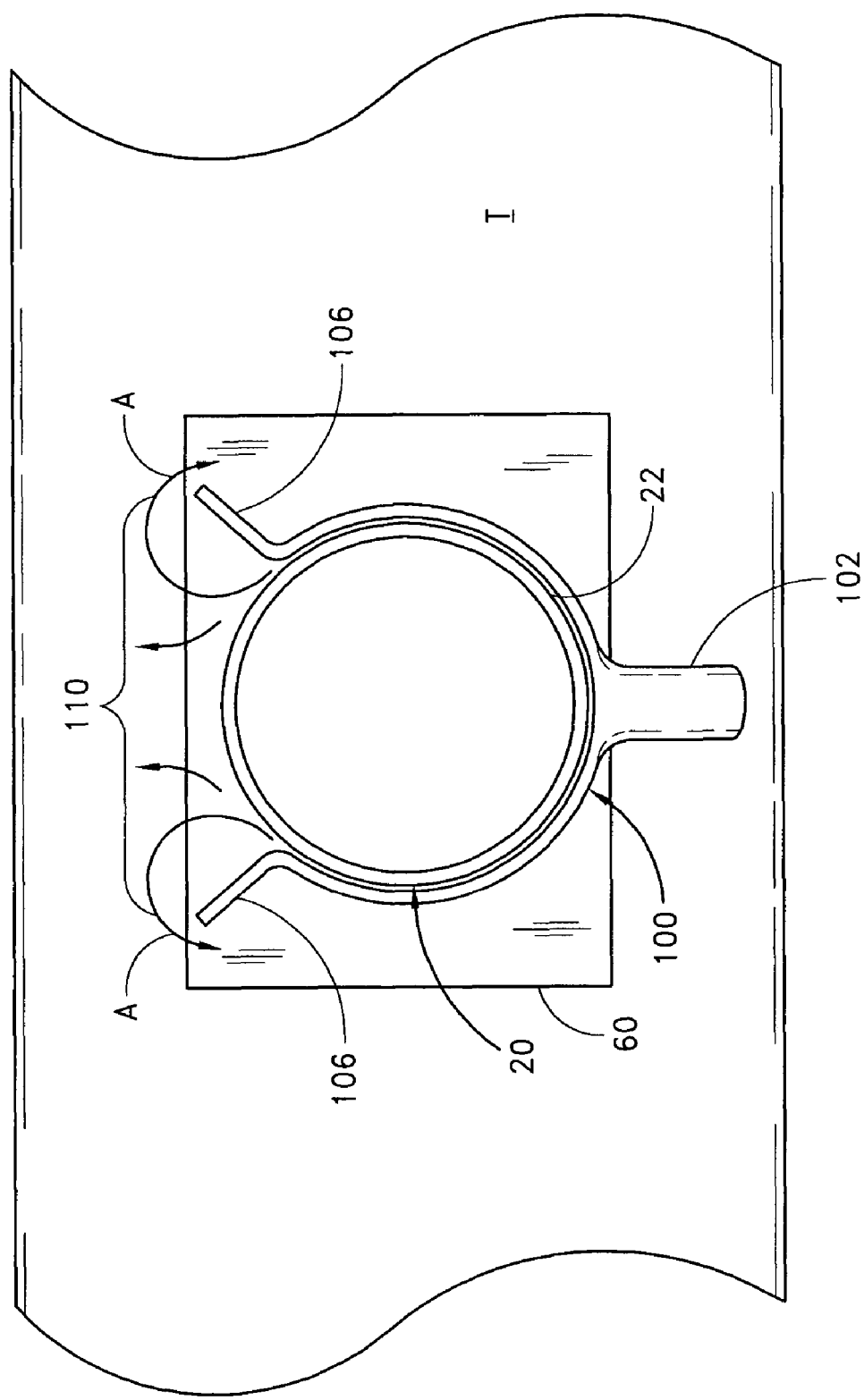
FIG. 12 shows the arrangement of FIG. 11 viewed from a proximal end of the apparatus.

FIGS. 11 and 12 show the use of the flow guide 100 to aid in the application of adhesive A when the patch applicator 20 has only angled access to the tissue T being closed. Prior to use of the patch applicator 20, the flow guide 100 is preferably moved longitudinally to the proximal-most position allowed by the slot 112. The flow guide 100 is secured in that position by the knob 120 so as not to interfere with application of the patch 60 and clearing of the field 80. After the field 80 has been cleared, the knob 120 is loosened and the flow guide 100 is moved longitudinally into contact with the tissue T and/or patch 60 and positioned so that the guide tabs 106 are in a generally upward-facing direction. It is to be understood that the guide tabs 106 can be oriented in any direction desired by the clinician such as, for example, rotated so that the flow path 110 opens to the side. After the flow guide 100 is in place, the knob 120 is tightened to secure the flow guide 100 in position and the adhesive A is injected through the outer lumen distal opening 50.

With reference specifically to FIG. 12, the flow guide 100 channels the adhesive A through the flow path 110 between the guide tabs 106. In the illustrated embodiment, the adhesive A is urged generally upwardly by the guide tabs 106. As shown, the adhesive A is directed into contact with the area of the patch 60 and surrounding tissue T generally above the patch applicator main body. As the adhesive A is injected, it flows beyond the guide tabs 106 and around the patch 60 into areas that may not have received adhesive coverage without the use of the flow guide. When the area above the patch applicator body has been satisfactorily coated with adhesive, the flow guide is withdrawn a short distance in order to allow adhesive to flow to the area vertically below the patch applicator body 22. Thus, adhesive A is directed in all desired directions.

Once the flow guide 100 has been used to direct adhesive in a chosen direction, the flow guide may be rotated. Rotation of the flow guide 100 relative to the main body 22 is limited by the pin 118 and transverse track 116 of the slot 112. Alternatively, the entire patch applicator 20 may be rotated with the flow guide 100. By rotating the flow guide to another position, adhesive A can be directed in another direction. This will result in better adhesive coverage over the patch 60 and tissue T surrounding the patch and improve the bond of the patch to the tissue.

The flow guide can be used at any time, and not just for angled approaches. For example, in certain applications, it may be desired to limit the volume of injected adhesive to as little as possible. The flow guide can be used to direct adhesive to specific areas around the patch in order to minimize the amount of adhesive that must be injected by the clinician. Thus, the flow guide may be used to ensure adequate adhesive coverage while using as little adhesive as possible.

Figure 13:
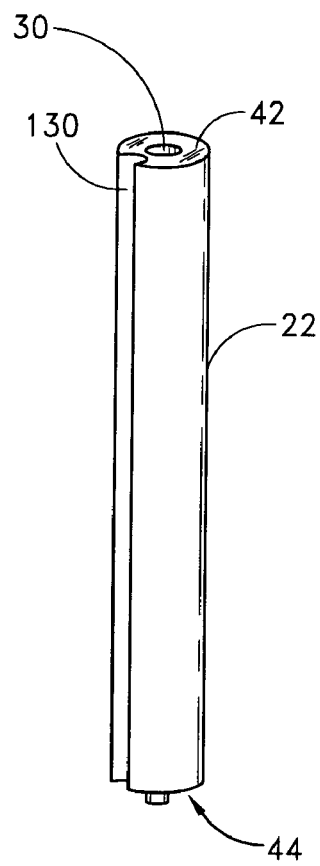
FIG. 13 shows a cut away portion of another embodiment of a patch applicator device having features in accordance with the present invention and including a groove.
Figure 14:
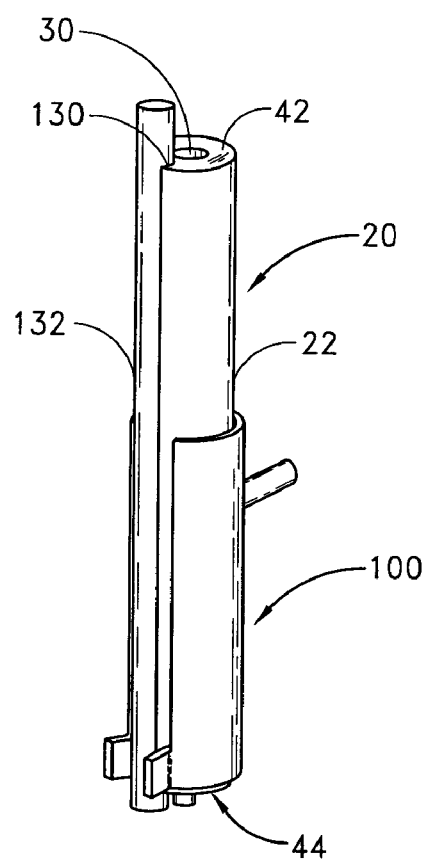
FIG. 14 shows the patch applicator device of FIG. 13 coupled with a flow guide and having an endoscope disposed in the groove.

With reference next to FIGS. 13 and 14, another embodiment of the patch applicator 20 is disclosed having a longitudinal groove 130 formed in the main body 22 and impinging into the outer lumen 42. The groove 130 is specially adapted to receive additional surgical instruments. For instance, with specific reference to FIG. 14, an endoscope 132 can be slid down the groove 130 to and beyond the distal tip 44 of the tubular main body 22. The endoscope 132 can be used to aid in locating the tissue wound, to check the position of the patch applicator device 20 and to verify that the wound has indeed been closed and sealed by the patch. Also, the endoscope 132 can be used to regulate and monitor distribution of adhesive around the patch and surrounding tissue. It is anticipated that a 2 mm endoscope will be especially suited for use in the present device.

In another embodiment, a heat probe or an ultraviolet ("UV") light probe can be slid down the groove 130 to the tip 44 of the main body 22 in order to aid in the curing or setting of the adhesive. Certain adhesives may develop a stronger bond or set quicker when exposed to heat or UV light. Therefore, the groove 130 may accommodate various probes to accomplish this task.

It is to be understood that more than one groove may be formed in the tubular body. Thus, the patch applicator can accommodate an endoscope, UV probe, and heat probe all at the same time.

The patch applicator device is preferably formed of surgical metals such as stainless steel. It is to be understood, however, that the device can also be made of other appropriate materials, such as, for example, medical plastics. Lightweight materials such as plastics may allow the device to be smaller and to have a relatively low profile, further facilitating the insertion of the device through trocars and cannulas. Plastic devices may also be more economical and allow for development of one-time-use products. Most preferably, the patch applicator is formed of a material that will not establish a bond with the chosen adhesive. Alternatively, the patch applicator device may have a coating, for example, a Teflon® coating, to inhibit bonding with the adhesive.

Certain internal bodily organs, such as the liver and intestines, will have a tendency to move when the patch applicator 20 applies pressure to the organ. This can present a problem because initial application of the patch to the wound may become difficult and unstable. Accordingly, an organ stabilizer 140 can be used to hold the organ in place while the patch applicator 20 applies pressure to a wound in the organ. Such an organ stabilizer 140 provides countertraction to hold the organ while the patch 60 is being applied.

Figure 15:
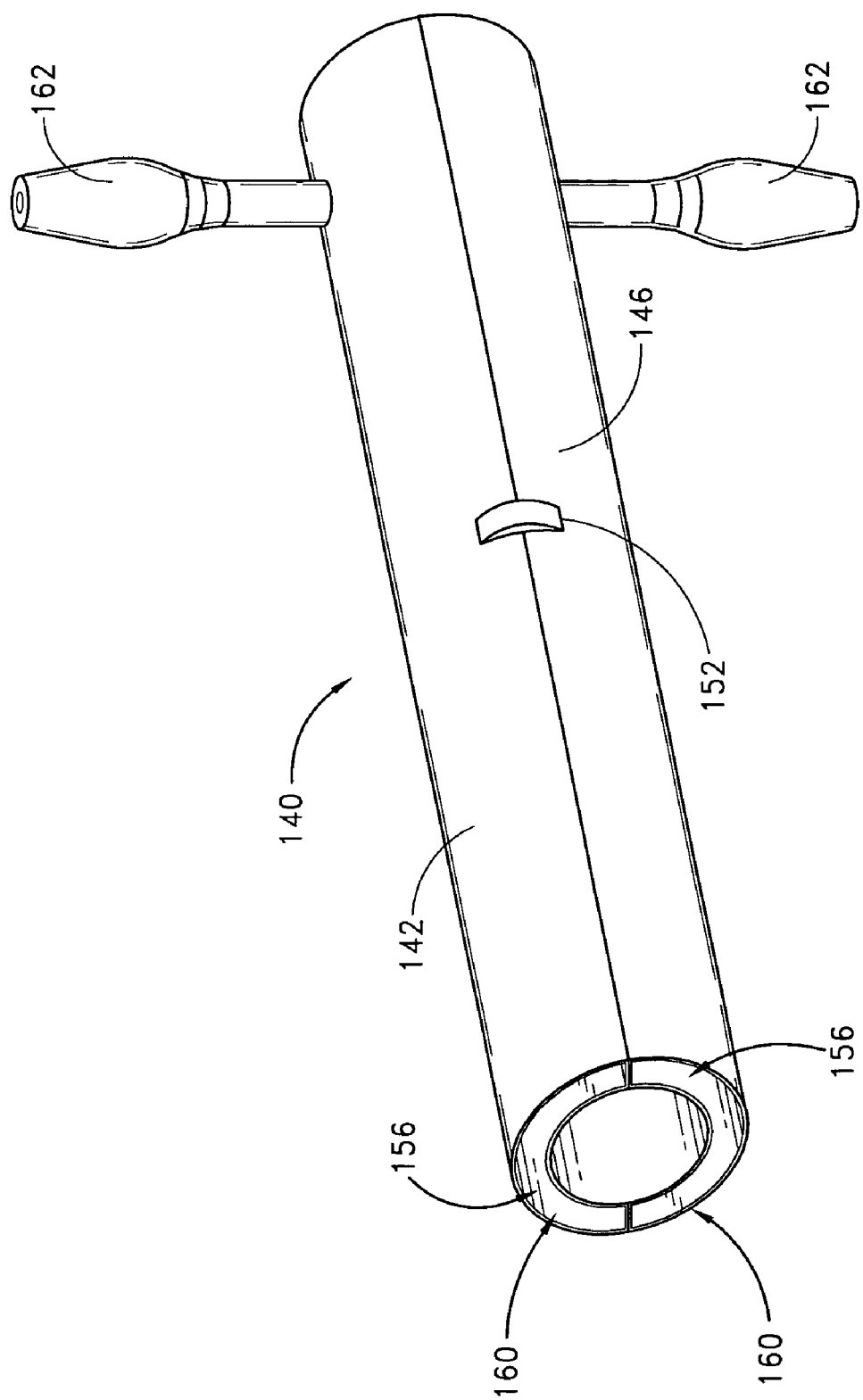
FIG. 15 shows a detachable organ stabilizer adapted for use in connection with the patch applicator device of FIG. 1.
Figure 16:
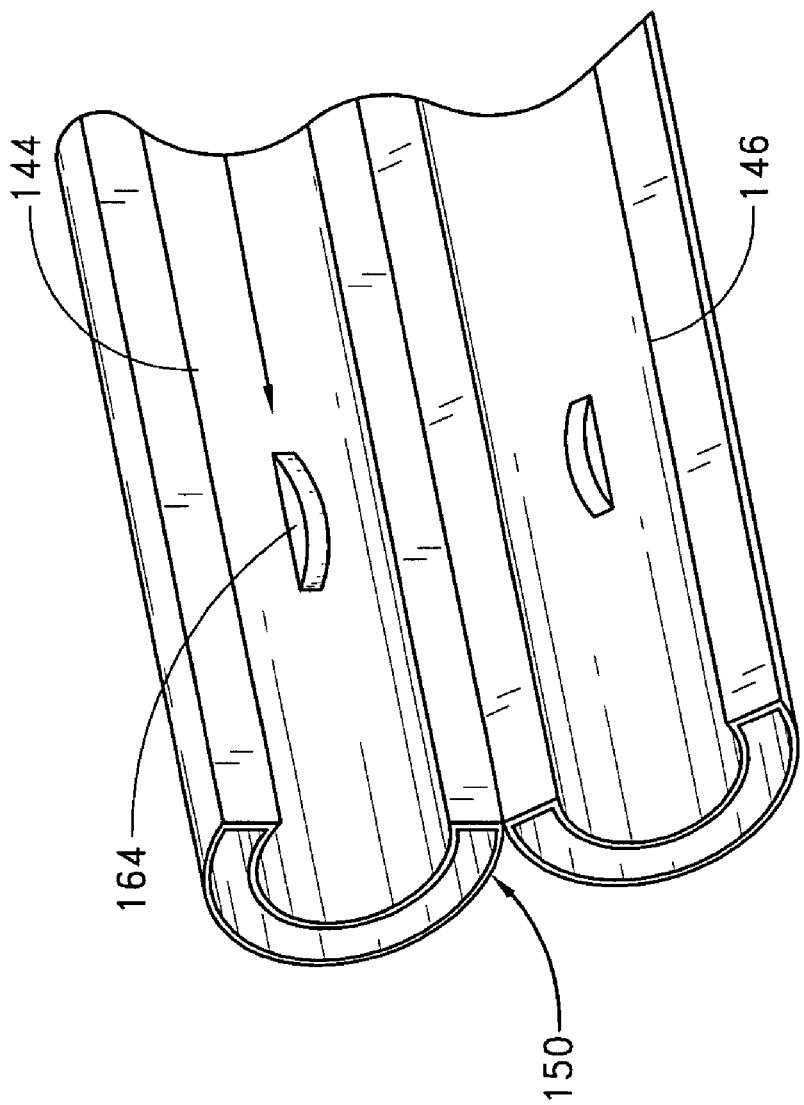
FIG. 16 shows a perspective view of the organ stabilizer of FIG. 15 showing two halves of the stabilizer in an open position.
Figure 17:
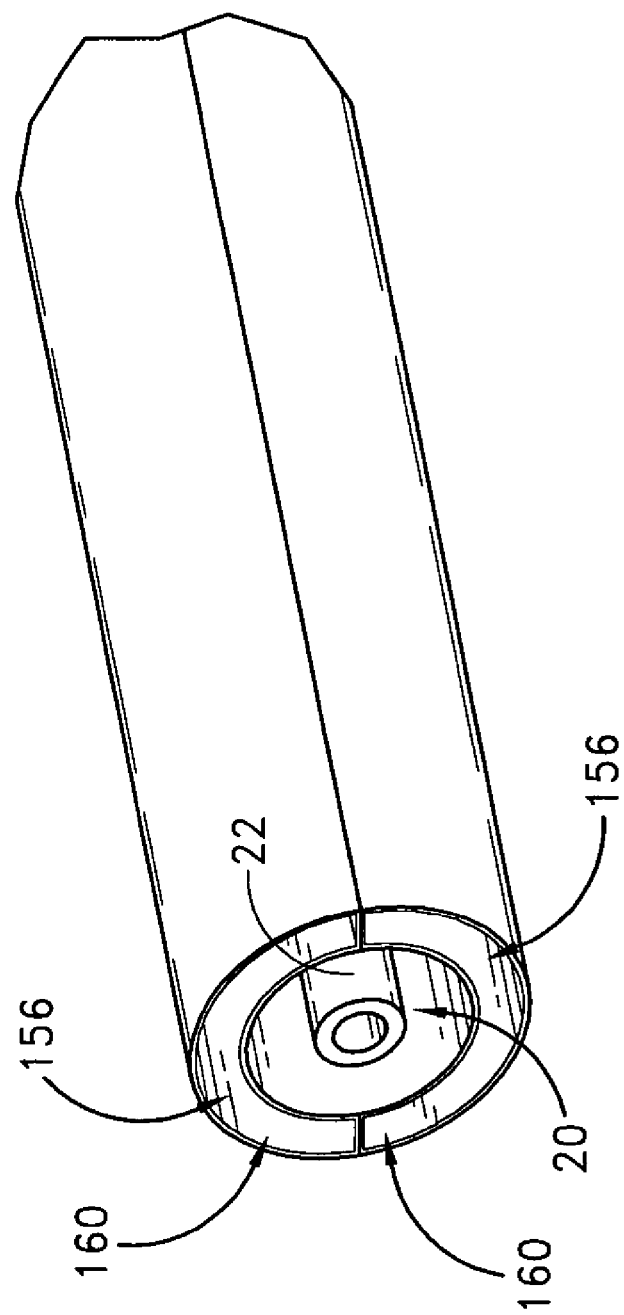
FIG. 17 shows the patch applicator device of FIG. 1 in combination with the organ stabilizer of FIG. 15.
Figure 18:
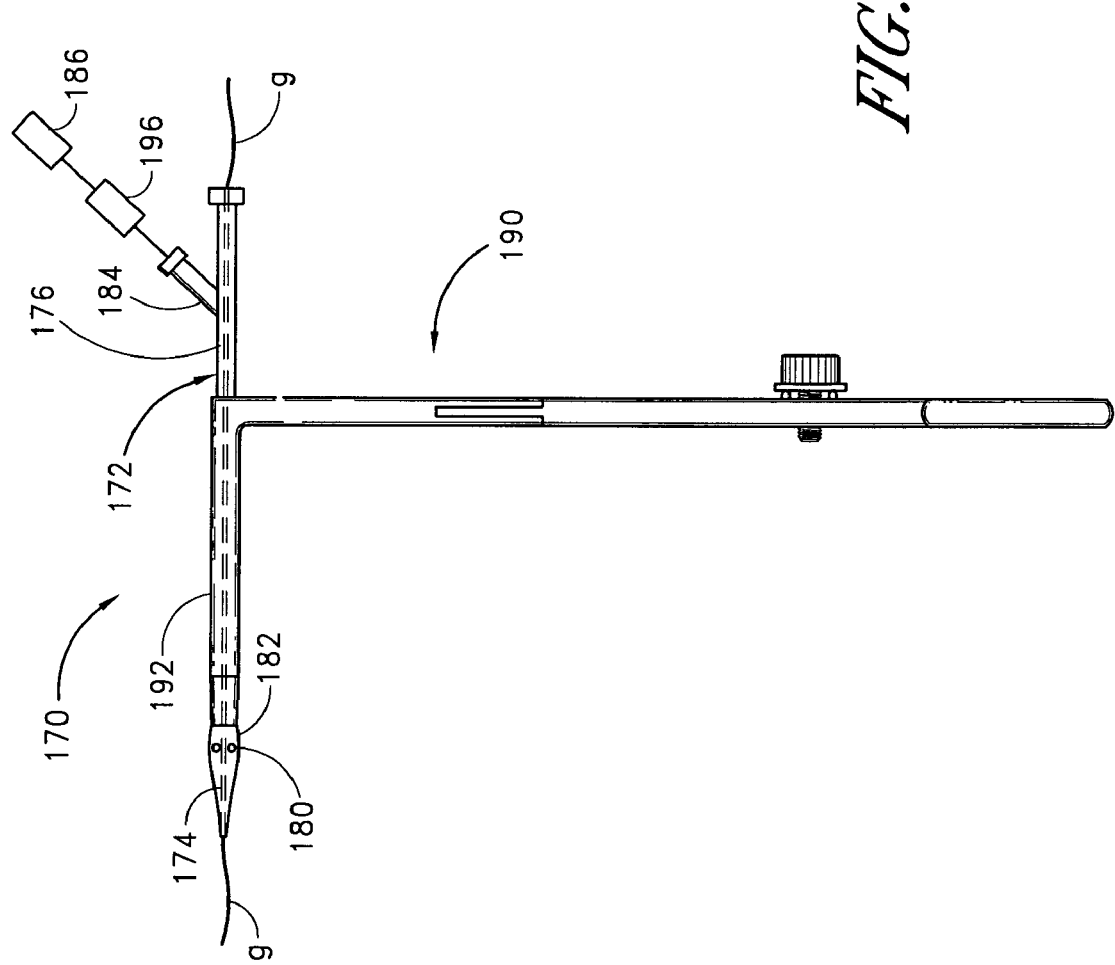
FIG. 18 is a side view of a vascular puncture locator apparatus.
Figure 19:
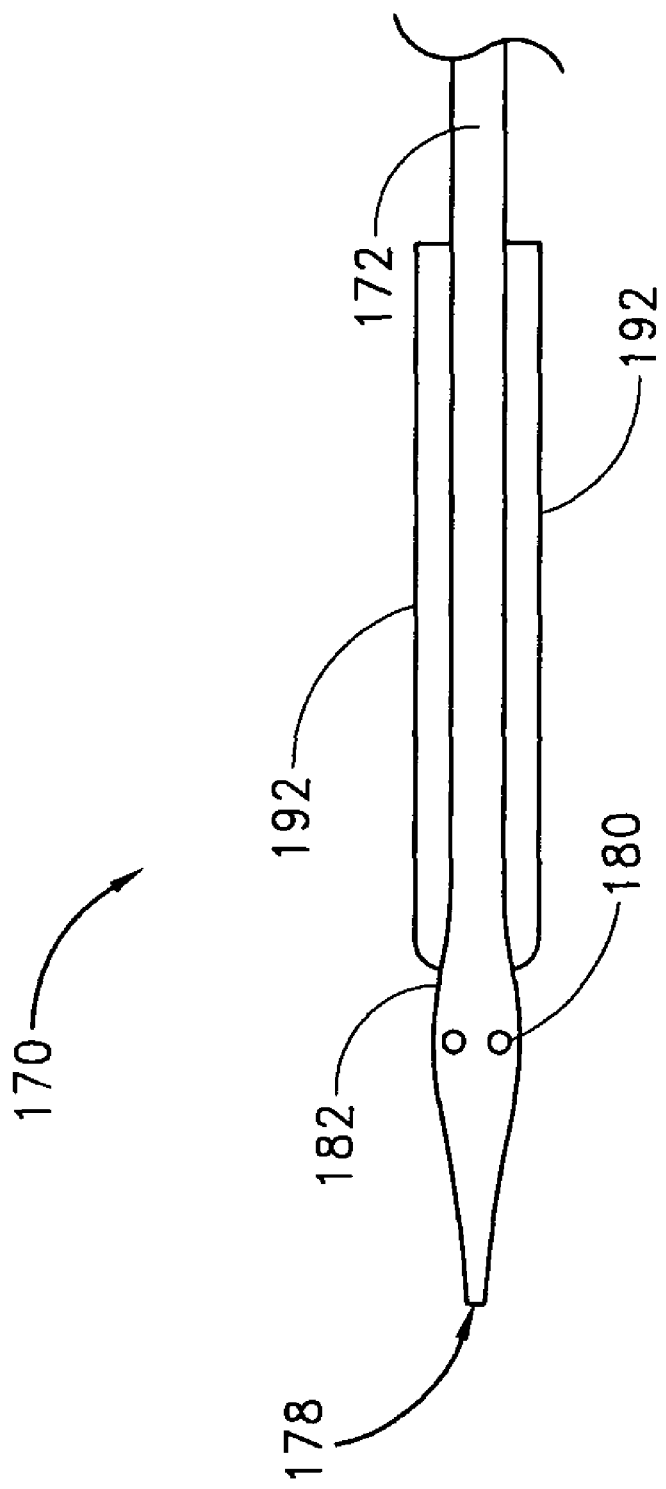
FIG. 19 is a side view of a distal portion of the apparatus of FIG. 18.

With reference next to FIGS. 15-17, a detachable organ stabilizer 140 is adapted for use with the applicator 20 of the present invention. The organ stabilizer comprises an elongate tubular body 142 which is formed by two adjoining halves 144, 146. The halves 144, 146 are preferably hinged 150 along a first side and are adapted to close upon one another, encircling the patch applicator 20. A latch 152 is provided to hold the halves 144, 146 closed. Each half preferably has a longitudinal lumen 156 having a vacuum suction port 160 at its distal end and a vacuum connector 162 near its proximal end. In use, a source of vacuum is connected to the vacuum connector 162 and a vacuum is pulled through each vacuum suction port 160.

As seen in FIG. 17, the organ stabilizer 140 is preferably sized to completely encircle a patch applicator 20 such as that discussed above. With reference back to FIG. 16, each half 144, 146 of the organ stabilizer body 142 has a positioning ridge 164. The positioning ridges 164 are adapted to contact the tubular body 22 of the patch applicator 20, thus positioning the patch applicator 20 generally centrally within the cross-section of the organ stabilizer 140, but allowing the applicator to move longitudinally relative to the stabilizer.

The organ stabilizer 140 draws a vacuum through the organ stabilizer suction ports 160. Thus, when the stabilizer suction ports 160 are brought into contact with the subject organ, the vacuum holds the organ in place. The patch applicator 20 can then be used to apply the patch to the wound in the organ and to apply pressure at the wound. The organ will not move out of the way when pressure is applied by the patch applicator because the organ stabilizer provides countertraction. Additionally, since the organ stabilizer halves 144, 146 distribute the counter traction force concentrically around the patch applicator, the organ is prevented from any twisting movement and is held securely when the patch is being applied.

It is to be understood that an organ stabilizer may be provided having a different construction than the illustrated embodiment. For example, an organ stabilizer may be provided which would connect slidably on a side of the patch applicator rather than concentrically surround the patch applicator. Additionally, a plurality of lumens could be included in the organ stabilizer and be arranged at various locations around the patch applicator.

The patch applicator device can be used alone or in conjunction with other apparatus that may aid the function of the device in certain applications. For example, in certain areas of the body, a vascular clamp may be used to temporarily stop blood flow through an artery or blood vessel in order to help keep the field relatively clear.

Additionally, a wound location apparatus may be employed to precisely locate and provide access to a wound in a patient's femoral artery to prepare the site for the patch applicator device. Such a wound location apparatus can comprise a dual lumen catheter combined with a retractor as disclosed in Applicants' patent entitled TISSUE OPENING LOCATOR AND EVERTER AND METHOD, U.S. Ser. No. 09/325,982, filed Jun. 4, 1999, now U.S. Pat. No. 6,287,322, which is hereby incorporated by reference in its entirety.

During angioplasty or angiography procedures, the patient's femoral artery is punctured to insert a catheter and guidewire "g" into the patient's vasculature. After the procedure is completed, the puncture wound "w" in the femoral artery must be closed and the bleeding through the puncture site in the artery stopped. Access to the femoral artery is provided by a small (for example, about one centimeter) incision through the patient's skin and on through the patient's musculature "m" to the blood vessel "v".

With next reference to FIGS. 18-21, the locator apparatus 170 includes a catheter 172 having a first lumen 174 adapted to accommodate the guidewire "g" and a second lumen 176 concentrically surrounding the first lumen 174. A distal-most opening 178 of the first lumen 174 is provided to accommodate the guidewire "g". Holes 180 are formed through the outer wall 182 of the catheter 172, opening into the second lumen 176. A connector 184 communicates with the second lumen 176 and is connectable to a source of suction 186, which communicates suction through the lumen 176 and through the holes 180.

The catheter 172 is adapted to be used in conjunction with a retractor 190 having separable elongate retractor arms 192. The elongate retractor arms 192 are mounted onto the catheter 172 so that distal ends of the arms 192 are positioned proximal of the holes 180 a distance approximately the same as a width of the artery wall 194, preferably about 0.5-2 mm. The catheter 172 is threaded over a guidewire "g" that has been previously inserted into the patient's femoral artery through the puncture wound "w". With the second lumen 176 attached to the source of suction 186 and the retractor 190 in place on the catheter 172, the assembly 170 is advanced over the guidewire "g" through the patient's tissue "m" so that a distal portion of the catheter 172 extends through the vascular puncture wound "w". The source of suction 186 draws bodily fluids through the distal holes 180 and through a viewing port 196. The viewing port 196 allows the clinician to identify the liquids being withdrawn, and can have any suitable structure such as, for example, clear tubing attached to the catheter, a translucent syringe, or even the catheter itself could have at least a portion which is translucent or substantially transparent.

Figure 20:
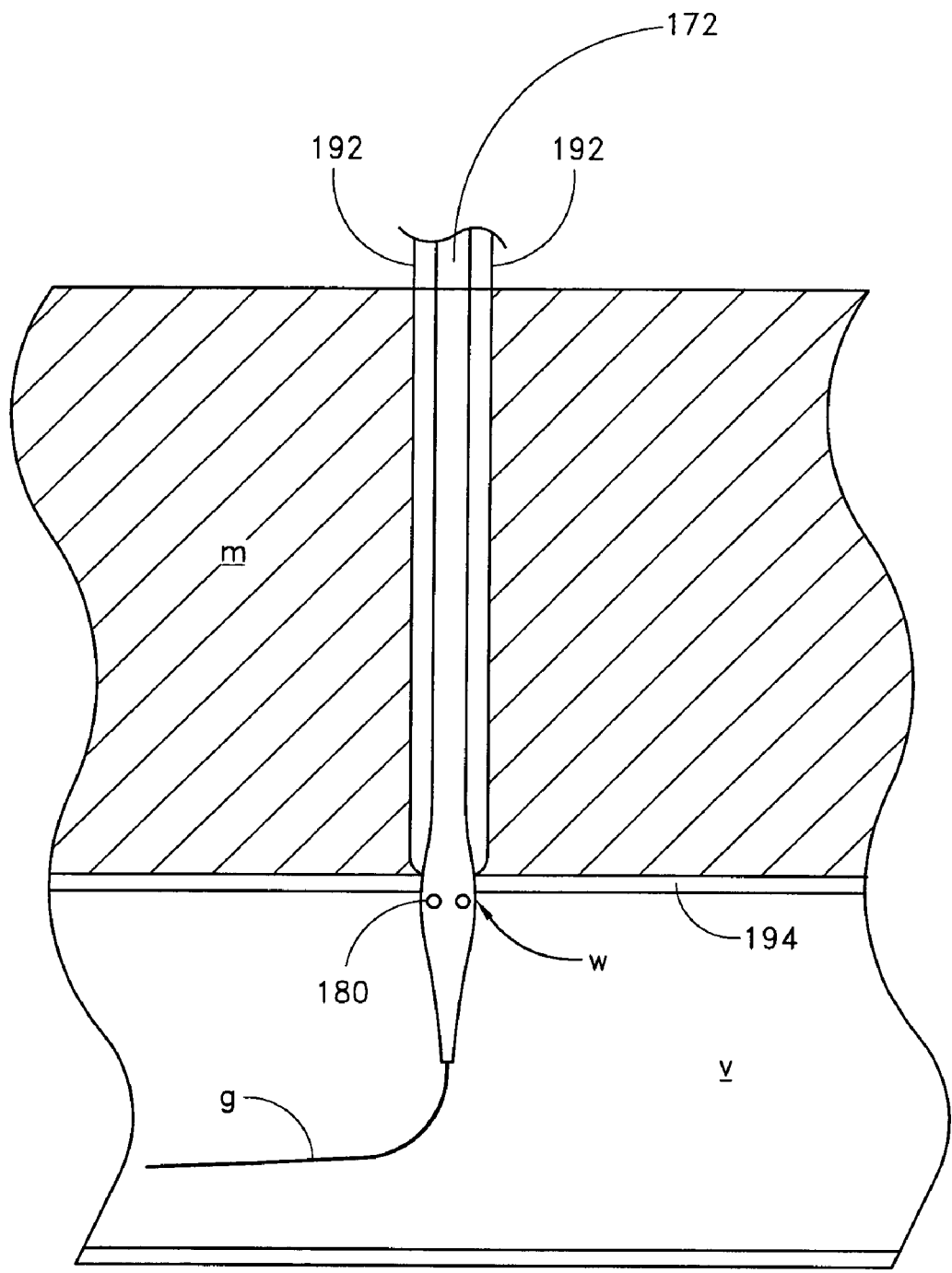
FIG. 20 shows the apparatus of FIG. 18 advanced over a guidewire into a blood vessel of a patient.
Figure 21:
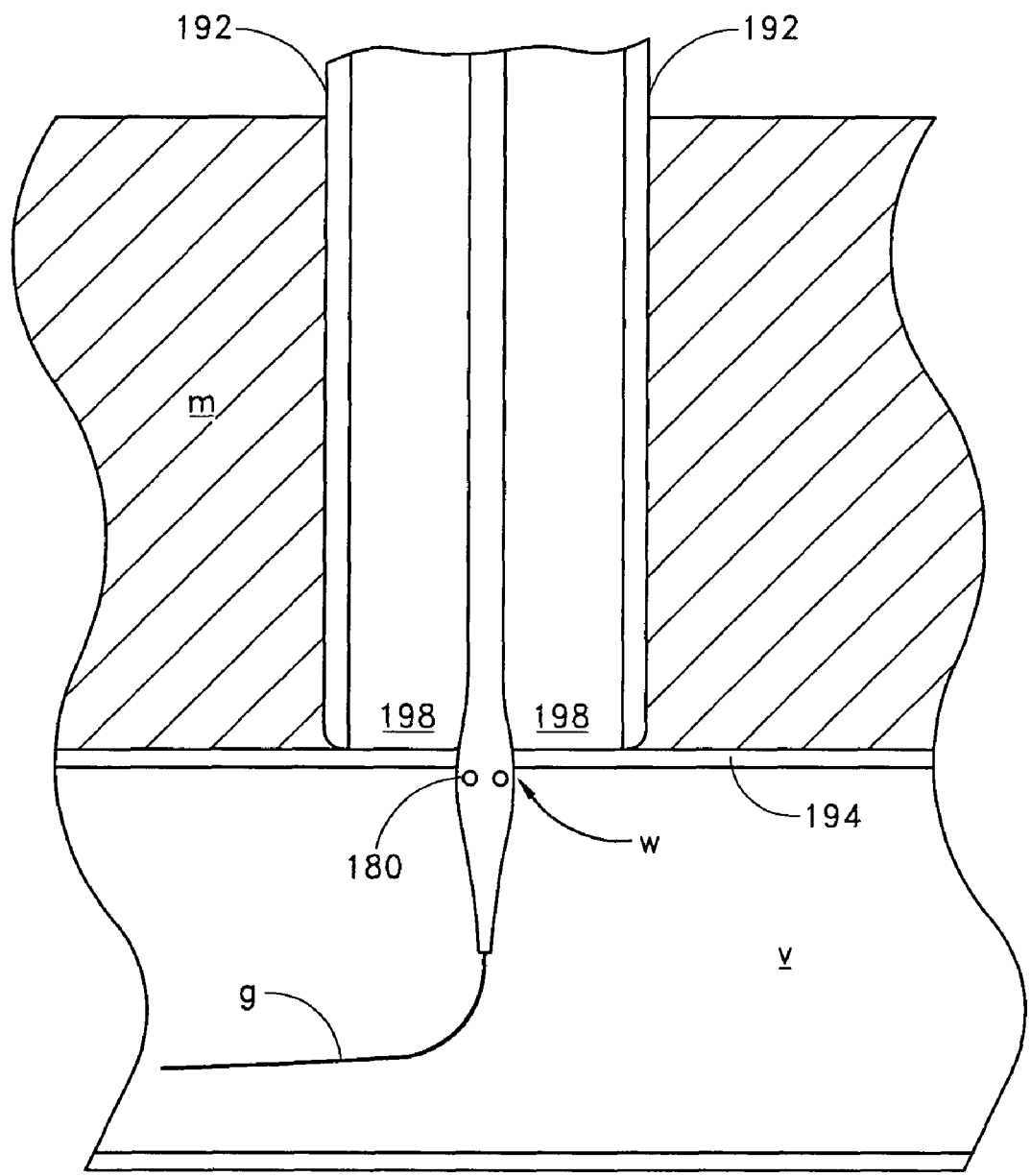
FIG. 21 shows the arrangement of FIG. 20 with the retractor arms open.

When the holes 180 pass the artery wall 194 and enter the blood vessel "v", as shown in FIG. 20, blood is drawn into the catheter 172 and is directed through the viewing port 196. Thus, when blood is observed in the viewing port 196, the clinician will know that the holes 180 have just passed into the puncture wound "w" and that the distal ends of the retractor arms 192 are positioned immediately adjacent the outer wall 194 of the artery. The retractor arms 192 are then separated as shown in FIG. 21, creating a field 198 around the puncture wound "w".

When a field 198 has been defined between the retractor arms 192, thus providing an access path to the puncture wound and the blood vessel surface surrounding the wound, a patch and patch applicator can be used to close the puncture wound in a manner as described above.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof Thus, it is intended that the scope of the present invention herein disclosed should not be limited by the particular disclosed embodiments described above, but should be determined only by a fair reading of the claims that follow.

What is claimed is:

1. A device for at least partially closing an opening in tissue, comprising:
    an elongate body comprising a first lumen having a first distal opening and a second lumen having a second distal opening, the lumens arranged so that a longitudinal space is defined between the first and second distal openings;
    a first connector adapted to provide access to the first lumen;
    a second connector adapted to provide access to the second lumen; and
    a non-inflatable wound cover member releasably connected to the elongate body at the first distal opening in a manner so that the wound cover member remains connected when the device is advanced toward a wound;
    wherein the device is configured so that, during advancement towards an opening in tissue and during operation, the first distal opening is permanently maintained at a position distal of the second distal opening, and the first and second lumens do not communicate with one another; and
    wherein the wound cover member and the elongate body are configured so that when the wound cover member is released from the first distal opening of the elongate body at or adjacent an opening in tissue, the wound cover member is wholly disconnected from the device.

2. A device as in claim 1,
    wherein the elongate body has a first portion comprising the first lumen and a second portion comprising the second lumen, and the first and second portions are rigidly connected to one another so as to always move as a single elongate unit.

3. A device as in claim 1 additionally comprising
    a flow guide comprising a flow guide body configured to be movably connected to the tissue closure device elongate body, a distal end of the flow guide body adapted to fit partially circumferentially around the elongate body and to define a flow path generally transverse to a longitudinal axis of the elongate body.

4. The device of claim 2, wherein the elongate portions extend generally parallel to a longitudinal axis of the elongate body.

5. The device of claim 4, wherein the first and second portions are arranged concentrically.

6. The device of claim 5, wherein the second portion is arranged concentrically around the first portion.

7. The device of claim 2, wherein the first and second portions are unitarily formed.

8. The device of claim 2, wherein the first lumen is connectable to a source of vacuum capable of drawing a vacuum through the first lumen.

9. The device of claim 8, wherein the wound closure member is held onto the first lumen distal opening by the vacuum.

10. The device of claim 3, wherein the flow guide comprises at least two guide tabs, and the flow path is defined between the guide tabs.

11. The device of claim 3, wherein the flow guide is longitudinally movable relative to the elongate body.

12. The device of claim 3, wherein the flow guide is rotationally movable relative to the elongate body.

13. The device of claim 3 additionally comprising a lock adapted to releasably secure the flow guide in a position relative to the elongate body.

14. A device as in claim 1 additionally comprising
an organ stabilizer configured to be movably attached to the elongate body;
wherein the organ stabilizer device comprises an elongate stabilizer body including a lumen having a distal opening, the lumen being connectable to a source of vacuum, the distal opening adapted to be engagable with bodily tissue to secure the tissue in place with the vacuum.

15. A device as in claim 1 additionally comprising
an organ stabilizer configured to be movably attached to the elongate body;
wherein the organ stabilizer device comprises an elongate stabilizer body having a ridge, and the ridge is configured to engage the tissue closure device elongate body so that the closure device elongate body is spaced from the elongate stabilizer body.

16. The device of claim 15, wherein the stabilizer body comprises a lumen having a distal opening adapted to be engagable with bodily tissue.

17. The device of claim 16, wherein the stabilizer body comprises a plurality of lumens.

18. The device of claim 1, wherein the second lumen is configured to communicate a flowing fluid therethrough.

19. The device of claim 1 additionally comprising a release rod sized and configured to slide through the first lumen and into contact with the wound cover member, the release rod being movable independent of the wound cover member.

20. A device as in claim 1 additionally comprising
a tissue stabilizer connected to the elongate body so as to be longitudinally movable relative to the elongate body;
wherein the elongate body is configured to push the wound cover member onto a body tissue at a desired location; and
wherein the tissue stabilizer is configured to apply traction in a direction generally opposed to the elongate body to a body tissue at a location at or adjacent the location of the wound cover member.

21. The device of claim 20, wherein the tissue stabilizer comprises a lumen, and the lumen is selectively connected to a source of suction.

22. The device of claim 21, wherein the tissue stabilizer comprises a plurality of lumens.

23. The device of claim 21, wherein the elongate body comprises a distal opening at the distal end, and a lumen communicating with the distal opening, the lumen being selectively attachable to a source of vacuum, and the wound cover member is releasably held onto the distal opening by the vacuum.

24. The device of claim 14, wherein the first and second portions are arranged adjacent one another and are rigidly connected so as to move as a single unit.

25. The device of claim 24, wherein the first and second portions are unitarily formed.

26. The device of claim 24, wherein the organ stabilizer extends circumferentially around the elongate body.

27. The device of claim 16, wherein the organ stabilizer body extends circumferentially around the elongate body.

28. The device of claim 2 additionally comprising a release rod, wherein the first lumen is adapted to slidably receive the release rod therein.

29. The device of claim 1, wherein the wound cover member has a maximum diameter that is greater than a diameter of the second lumen distal opening.

30. The device of claim 1, wherein the first connector is adapted to connect to a source of vacuum so as to draw a vacuum through the first lumen.

31. The device of claim 30, wherein the wound closure member is held onto the first lumen distal opening by the vacuum.

32. The device of claim 30, wherein the second connector is adapted to selectively connect to a source of vacuum so as to draw a vacuum through the second lumen.

33. The device of claim 1, wherein the second connector is adapted to selectively connect to a source of irrigation fluid.

34. The device of claim 1, wherein the second connector is adapted to selectively connect to a source of flowable adhesive so that flowable adhesive may flow through the second lumen and out the second distal opening.

35. The device of claim 1, wherein the second connector defines a second connector lumen, and an axis of the second connector lumen is disposed in a direction generally transverse to an axis of the second lumen.

36. The device of claim 1, wherein the wound cover member does not engage any portion of the device other than the first distal opening.

37. The device of claim 36, wherein the wound cover member substantially does not extend proximally beyond the first distal opening.

38. The device of claim 1, wherein the wound cover member is cuttable.

39. The device of claim 1, wherein the second lumen terminates at the second distal opening.

40. The device of claim 39, wherein the second distal opening lies in a plane substantially normal to a longitudinal axis of the second lumen.

41. The device of claim 40, wherein the wound cover member is sized and configured to block the first distal opening when connected to the elongate body and a portion of the wound cover member extends outwardly from the first distal opening in a direction generally transverse to the first lumen longitudinal axis, and wherein the second distal opening opens toward the portion of the wound cover member.

* * * * *